US006993378B2

(12) United States Patent
Wiederhold et al.

(10) Patent No.: US 6,993,378 B2
(45) Date of Patent: Jan. 31, 2006

(54) IDENTIFICATION BY ANALYSIS OF PHYSIOMETRIC VARIATION

(75) Inventors: Mark D. Wiederhold, San Diego, CA (US); Steven A. Israel, Fairfax, VA (US); Rodney P. Meyer, Burke, VA (US); John M. Irvine, Somerville, MA (US)

(73) Assignee: Science Applications International Corporation, San Diego, CA (US)

( * ) Notice: Subject to any disclaimer, the term of this patent is extended or adjusted under 35 U.S.C. 154(b) by 530 days.

(21) Appl. No.: 10/178,839

(22) Filed: Jun. 25, 2002

(65) Prior Publication Data

US 2003/0135097 A1    Jul. 17, 2003

Related U.S. Application Data

(60) Provisional application No. 60/300,070, filed on Jun. 25, 2001.

(51) Int. Cl.
*A61B 5/0402*    (2006.01)

(52) U.S. Cl. ..................... 600/509; 382/115
(58) Field of Classification Search ............... 600/508, 600/509, 529, 532; 382/115
See application file for complete search history.

(56) References Cited

U.S. PATENT DOCUMENTS

| | | | |
|---|---|---|---|
| 5,544,649 A | 8/1996 | David et al. | |
| 5,719,950 A | 2/1998 | Osten et al. | |
| 5,737,439 A | 4/1998 | Lapsley et al. | |
| 6,112,224 A | 8/2000 | Peifer et al. | |
| 6,173,068 B1 | 1/2001 | Prokoski | |
| 6,208,264 B1 * | 3/2001 | Bradney et al. | ............. 340/5.2 |
| 6,309,342 B1 | 10/2001 | Blazey et al. | |
| 6,616,613 B1 * | 9/2003 | Goodman | ............ 600/504 |

OTHER PUBLICATIONS

Irvine et al., "Heart Rate Variability: A New Biometric For Human Identification", presented at International Conference on Artificial Intelligence, Jun. 25-28, 2001, Las Vegas, NV.

Mateo et al., "Improved Heart Rate Variability Signal Analysis from the Beat Occurrence Times According to the IPFM Model", IEEE Transactions on Biomedical Engineering, Aug. 2000, pp 985-996, vol. 47, No. 8.

Yoshiya et al., "Spectrophotometric monitoring of arterial oxygen saturation in the fingertip", Med. & Biol. Eng & Comput., Jan. 1980, pp 27-32, vol. 18.

Task Force of the European Society of Cardiology and the North American Society of Pacing and Electrophysiology, Special Report, Heart Rate Variability, Standards of Measurement, Physiological Interpretation, and Clinical Use, American Heart Association, 1996, pp 1043-1065.

Kundu et al., "Knowledge-based ECG interpretation: a critical review", Pattern Recognition Society, 2000, pp 351-373.

* cited by examiner

*Primary Examiner*—Scott M. Getzow
(74) *Attorney, Agent, or Firm*—Banner & Witcoff, Ltd.

(57) ABSTRACT

Methods involving extraction of information from the inherent variability of physiometrics, including data on cardiovascular and pulmonary functions such as heart rate variability, characteristics of ECG traces, pulse, oxygenation of subcutaneous blood, respiration rate, temperature or $CO_2$ content of exhaled air, heart sounds, and body resonance, can be used to identify individual subjects, particularly humans. Biometric data for use in the methods can be obtained either from contact sensors or at a distance. The methods can be performed alone or can be fused with previous identification algorithms.

32 Claims, 26 Drawing Sheets

Inhalation  Exhalation

Note change in apparent
temperature at the nostrils

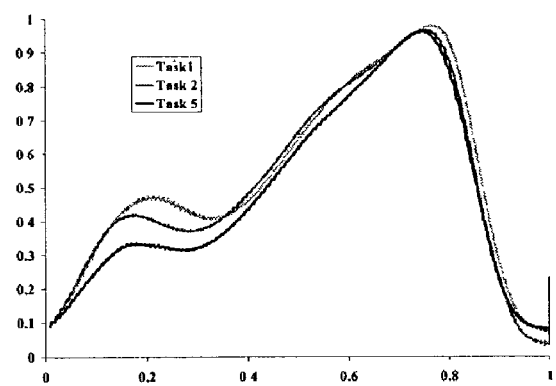 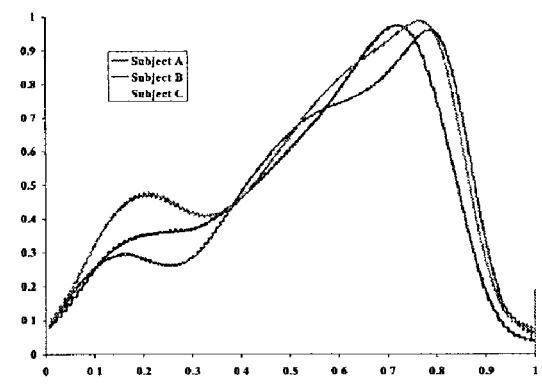
FIG. 15A
FIG. 15B

IDENTIFICATION BY ANALYSIS OF PHYSIOMETRIC VARIATION

This application claims the benefit of and incorporates by reference co-pending provisional application Ser. No. 60/300,070 filed Jun. 25, 2001.

FIELD OF THE INVENTION

The invention is related to the use of individual variations in physiometric data to identify individuals. More specifically, the invention is related to the analysis of data such as cardiovascular and/or respiratory data and the identification of humans based on individual variations thereof.

BACKGROUND OF THE INVENTION

Biometric techniques, such as face recognition, finger print analysis, iris recognition, and voice recognition have emerged as methods for automatically identifying individuals. These techniques can be implemented to provide automated security for facilities, to restrict access to computer networks, or to verify identification for online transactions.

Traditional biometric techniques, however, provide only a "snapshot" of data that can be represented in an image format. There is a need in the art for more sensitive and accurate biometric identification techniques.

SUMMARY OF THE INVENTION

In these and other embodiments the invention provides methods and apparatuses useful for verification of identity, which may be used for a variety of purposes such as a prerequisite to entry of secured facilities, use of restricted information systems, and conduct of business or legal activities, as well as identification of unknown individuals and confirmation of the identity of known individuals.

For example, according to aspects of the present invention, a new biometric technique may be used that is based on signals such as heart rate variability and/or respiration processes. Traditional biometrics, such as face recognition, fingerprint identification, and iris recognition, rely on a "snapshot" of data that can be represented in an image format. The biometric proposed here may exploit information about a dynamic physiological process that can be interrogated using sensors such as non-imaging sensors. Certain features can be extracted from the data, and those features can uniquely correspond to, and identify, individuals. This is also a very robust technique that can be accurate even under varying conditions. For instance, while a person's heart rate can vary with mental and emotional state, the shape of a signal corresponding to the heartbeat is for the most part unique to that person, or varies in a way that is unique to that person

BRIEF DESCRIPTION OF THE DRAWINGS

The foregoing summary of the invention, as well as the following detailed description of preferred embodiments, is better understood when read in conjunction with the accompanying drawings, which are included by way of example, and not by way of limitation with regard to the claimed invention.

FIG. 11. Example of suppression of a 60 Hz artifact.

FIG. 15. Average normalized wave from pulse oximeter data. FIG. 15A, variability across tasks within a single subject. FIG. 15B, variability across subjects for a single task.

FIG. 16. Graphs showing RR interval determination.

FIG. 17. Graphs showing power spectral density of R peaks.

FIG. 18. Heart rate variability from three different subjects.

FIG. 19. Graphs showing variation in RR interval for subject 300.

FIG. 20. Waterfall plots for three different subjects obtained by stacking information temporally and aligning the R wave peaks by heart beat.

FIG. 21. Power spectral density from two individuals speaking identical phrases.

FIG. 22. Graphs of separability for training and test using 512 input sample segments, ~0.02 second, generated using Mahalanobis distance as a discriminator.

FIG. 23. Graphs of separability for training and test using 1024 input sample segments, ~0.05 seconds, generated using Mahalanobis distance as a discriminator.

FIG. 24. Graphs of separability for training and test using 2048 input sample segments, ~0.09 seconds, generated using Mahalanobis distance as a discriminator.

DETAILED DESCRIPTION OF ILLUSTRATIVE EMBODIMENTS

Figure 1:
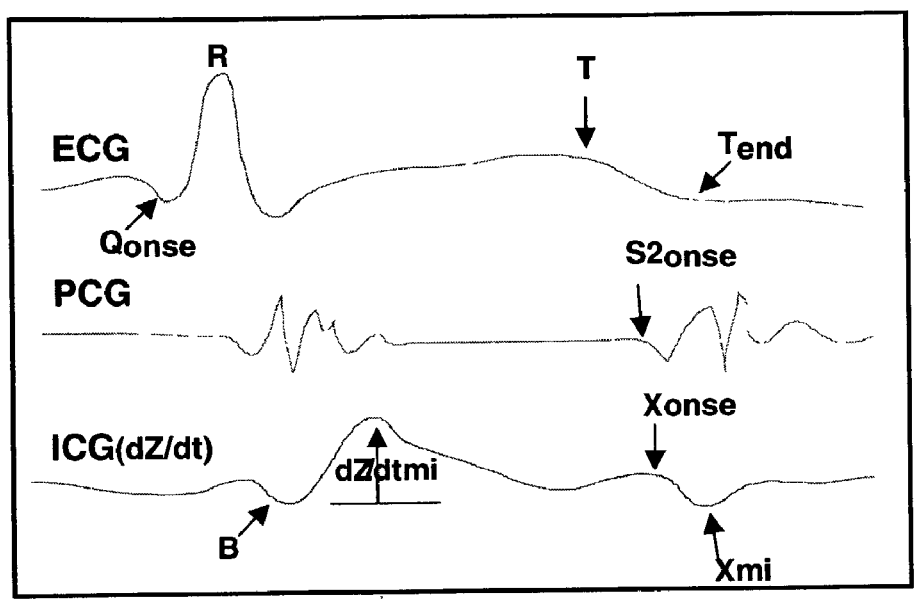
FIG. 1. Examples of characteristic electrocardiogram (ECG), phonocardiogram (PCG), and impedance cardiogram (ICG) signals. The ICG is the first derivative of the pulsatile thoracic impedance signal (dZ/dt). The relevant waveform events used to derive stroke volume, systolic time intervals, and other estimates of cardiac inotrophy are depicted.

The invention provides methods useful for verification of identity as a prerequisite to entry of secured facilities, use of restricted information systems, and conduct of business or legal activities, as well as identification of unknown individuals. These methods complement traditional identification techniques and can be fused with traditional biometric techniques to provide improved performance. Such fusion-based systems would be much harder for unauthorized personnel to circumvent or defeat.

During manunalian development, a series of genetically programmed steps leads to the growth of organs and physiologically interactive systems. For example, although a "human blueprint" exists, anatomical differences are a rule, forcing medical students to learn about the many "variants" of anatomical structure. Anatomical differences are already exploited in biometrics such as fingerprints and iris patterns. These anatomical differences can be further used to identify individual functional and physiological biometrics.

The various illustrative methods and apparatuses described below involve one or more of several unique processing stages. The methods may involve high temporal resolution data collection that can resolve the difference among the components of the heartbeats. Attribute feature sets may further be provided to characterize individuals. The feature extraction methods are space-robust and quasi-invariant to state of anxiety. In general, robust statistical processing of a subject permits quantitative analysis of performance.

Underlying Physiological Principles

The physiological "set point" for humans and other mammals is a unique quality with a number of diverse inputs, which gives rise to the distribution seen in measures such as resting heart rate, resting respiratory rate, and temperature. As the understanding of human physiology and the physiology of other mammals has advanced, the increasing complexity of physiological control has become apparent. The illustrative identifying biometrics disclosed herein are based on the following underlying physiological principles.

The control of mammalian physiological systems results from a complex interaction of neural and musculoskeletal inputs combined with a family of effector molecules. Some of the physiological controllers are under voluntary control, while others are involuntary. The action of the parasympathetic and sympathetic nervous systems of considerable interest. These two neurally and chemically mediated systems act as opposing regulators to maximize physiological performance. For example, the sympathetic nervous system increases heart rate by the release of epinephrine, while the parasympathetic nervous system slows the heart rate by action of the vagus nerve.

Experience in the medical community indicates that patterns observed in electrocardiograms (ECGs) are unique to an individual. Indeed, doctors offer anecdotal evidence that patients can be identified by their ECG traces. Analysis of available ECG data is consistent with this belief While direct measurement of the ECG may not provide a practical biometric for human identification, other less direct measures of heart rate and/or other cardiac parameters are possible and provide the same unique identifier for individuals.

Similar arguments, based on experience in the medical community, suggest that respiration may offer a similar unique identifier. The physiological processes that affect respiration (the sympathetic nervous system, lung capacity, structure of the respiratory passages, etc.) suggest that respiration may also provide a unique identifier for an individual.

Finally, a large body of literature exists on speaker recognition. The fundamental frequencies associated with speech depend on the mechanism for generating the sounds and the shape and size of body cavities in which the sound resonates. Analysis of a small set of data reinforces the concept of human identification based on the fundamental frequencies associated with the speaker.

Biometric Measurements

The illustrative biometrics disclosed herein may not only have the capability to lead to individually recognized patterns, but also may be measured at a distance (using standoff techniques), providing the potential for non-intrusive means of identifying individuals.

Heart Rate Variability

"Heart rate variability" (HRV) is the temporal difference between successive heartbeats, and is controlled by a variety of physiological inputs. Some of these inputs include biochemical, neural, and hormonal. Task Force of the European Society of Cardiology and the North American Society of Pacing and Electrophysiology, 1996; Kundu et al., 2000; Mateo & Laguna, 2000. HRV can be measured by a variety of methods such as using standard electrocardiogram (ECG) contact leads and also can be approximated by measuring the pulse at the extremities or by other means such as a pulse oximeter. Each method may record each heartbeat, and/or the interval between beats. FIG. 1 shows the correlation of contact sensors with an impedance cardiogram, which indicates heart contraction, with the largest peak formed by the contraction of both right and left ventricles. Feature extraction procedures described below show clear evidence of separability among individuals. These features are stable for an individual across tasks that are designed to evoke varying mental and emotional responses from the participants. Thus, HRV provides a viable biometric for uniquely identifying individuals.

A standoff technique may be used to take advantage of an older method for measuring heart function, the ballistocardiogram. Newer radar techniques can be used at a distance to determine cardiac function as well as heart rate variability. Previous research suggests that the heartbeats can be discerned in the signal acquired by radar. Greneker, 1997. This strong contraction is also detectable by a radar technique.

Multiple contact measurements associated with heart rate and circulation can be acquired, each measuring one or more of the same or different physiological phenomena. These phenomena include, but are not limited to, mechanical activity of the heart, fluctuation of the skin surface associated with the pulse, and change in blood oxygen levels associated with the pulse.

Pulse can be measured at various body locations, such as the carotid, radial, or femoral arteries. Means of contact pulse measurements include measurement of electrical potential via electrocardiogram, measurement of acoustic wave pressure, and pulse oximetry. Laser vibrometry offers one method for measuring pulse at a distance. Unlike radar, however, a laser requires line-of-sight to the target area.

Figure 2:
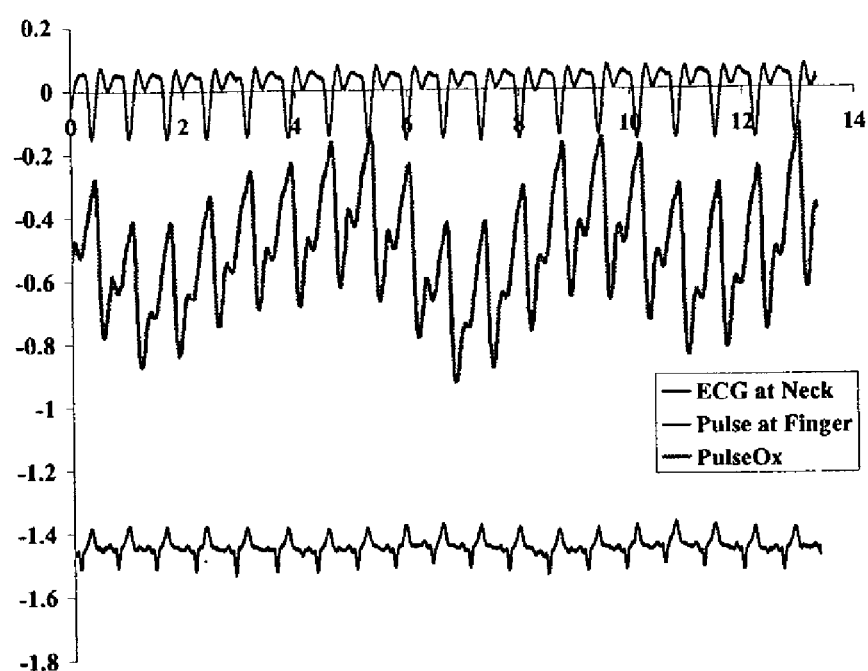
FIG. 2. Tracings of simultaneous ECG, heart rate, and pulse oximeter data, showing the strong relationship among the three signals.

Pulse oximetry offers a simple, direct method for acquiring information about heart rate variability. Yoshiya et al., 1980. Acquisition of simultaneous ECG, heart rate, and pulse oximeter data shows the strong relationship among the three signals (FIG. 2). The collection of pulse oximetry data is relatively simple and non-invasive. The bonding of oxygen to hemoglobin affects the color properties of the blood. Specifically, differential coloring is associated with deoxyhemoglobin (Hb) and oxyhemoglobin ($HbO_2$). By illuminating the skin at the appropriate wavelengths (e.g., about 660 nm light, where the absorbance of deoxyhemoglobin and hemoglobin differ, and, e.g., about 805 nm near infrared light, where the absorbance of both hemoglobin species is the same) and measuring the two signals, it is possible to estimate the oxygen level in the blood. Consequently, the pulse oximeter offers a simple method for observing heart rate variability. Contact pulse oximeter measurements provide a good signal. Thus, standoff sensing may be achieved, for example, using an active illumination source.

Respiration Patterns

Respiration rate and/or functional parameters can be evaluated by movement of the air at the nares, expansion of the chest, and change in temperature at the nares. Respiration information can be acquired, for example, by direct measurement of the temperature change associated with inhalation and exhalation, by using a pressure transducer on the chest to measure changes associated with breathing, and/or by using a pressure transducer at the heart to capture a combined signal associated with the heartbeat and/or respiration. In the specific examples below, we used two types of contact sensors, one on the nose and one on the chest, to measure breathing differences.

Figure 7:
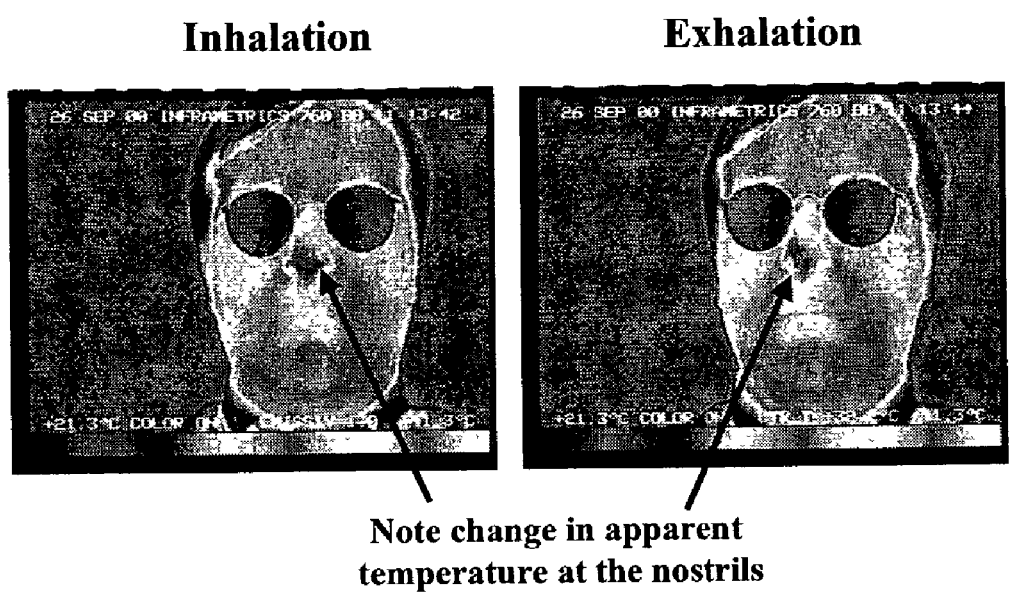
FIG. 7. Long-range infrared video image of temperature change associated with inhalation and exhalation near the nose.

A variety of long-range standoff sensors may be used, including but not limited to radar, laser, and thermal imagery. A long range standoff measure may use, for instance, an infra-red camera with video capability. A liquid nitrogen cooled device should be able to pick up temperature changes around the nares corresponding to respiratory rate, as well as actual breath plumes, which would relate to respiratory functional parameters. As discussed above, previous research indicates that, at the right frequency and power, radar can be used to measure both heartbeat and respiration. A second approach, using the laser, requires a target area that moves with inhalation and exhalation. While clothing per se may not pose a problem, loose clothing could attenuate the signal of interest. A third technique, which may prove the easiest approach operationally, is to collect thermal video data. Experiments have shown that the temperature changes associated with inhalation and exhalation are evident in thermal infrared imagery (FIG. 7).

Body Resonance

Body resonance, which results from the propagation of voice and sound (breathing, heart sounds, gastrointestinal sounds, etc.) through solid and liquid organs and body structures, is profoundly affected by anatomical differences. Contact microphones placed over the larynx, and/or at one or more other sites (over solid, liquid and/or air filled cavities), such as the lung fields and sinuses, will pick up multiple frequencies. A standoff technique using a microphone array or laser method could pick up these individual frequencies. The major challenge of standoff measurements is the rapid decay of the signal as a function of distance. Dish microphones offer one relatively simple approach to collecting the acoustic data at a distance. At larger distances, an array of microphones may be used to acquire the signal.

A comparison between contact and standoff techniques for taking biometric measurements is shown in Table 1. It should be noted that Table 1 is merely illustrative, and other sensors and techniques may be used for each measurement than those indicated.

TABLE 1

Illustrative Relationship Between Contact Data and Sensing at a Distance.

| Measurement | Contact/ Proximity Sensor | Distance Sensing Technique |
| --- | --- | --- |
| Respiration | Pressure Transducer | Laser vibrometer |
| Heartbeat | | Laser vibrometer |
| Respiration and heartbeat | Pressure Transducer | Radar |
| Pulse in finger | Pressure Transducer | Differential light absorption (oximetry) |
| Respiration (nose) | Temperature | Thermal IR Sensor |
| $ETCO_2$ | $CO_2$ | Laser spectroscopy |
| Pulse Oximetry | Pulse Oximeter | Differential light absorption (oximetry) |
| Body resonance (throat) | Microphone | Dish microphone Laser vibrometer |
| Body Resonance (multiple sites) | Microphone | Dish microphone Laser vibrometer |

ECG Data Processing

Collecting a relatively short sequence of ECG data, i.e., for approximately less than 1, 10–20, 7–8, 5–10, or 10–25 second (e.g., 3, 5, 6, 7, 8, 9, 10, 15, 20, or 25 seconds, provides a considerable amount of information. As the number of heartbeats collected increases, the sample becomes more statistically significant. However, identification may be achieved using data collected for less than one second or for a single heartbeat. A predetermined number of heartbeats also can be collected. Parametric statistics can also be applied to perform identification with a Gaussian distribution. Such statistical processing may allow for quantitative, easily derived, and understood performance measures.

Figure 3:
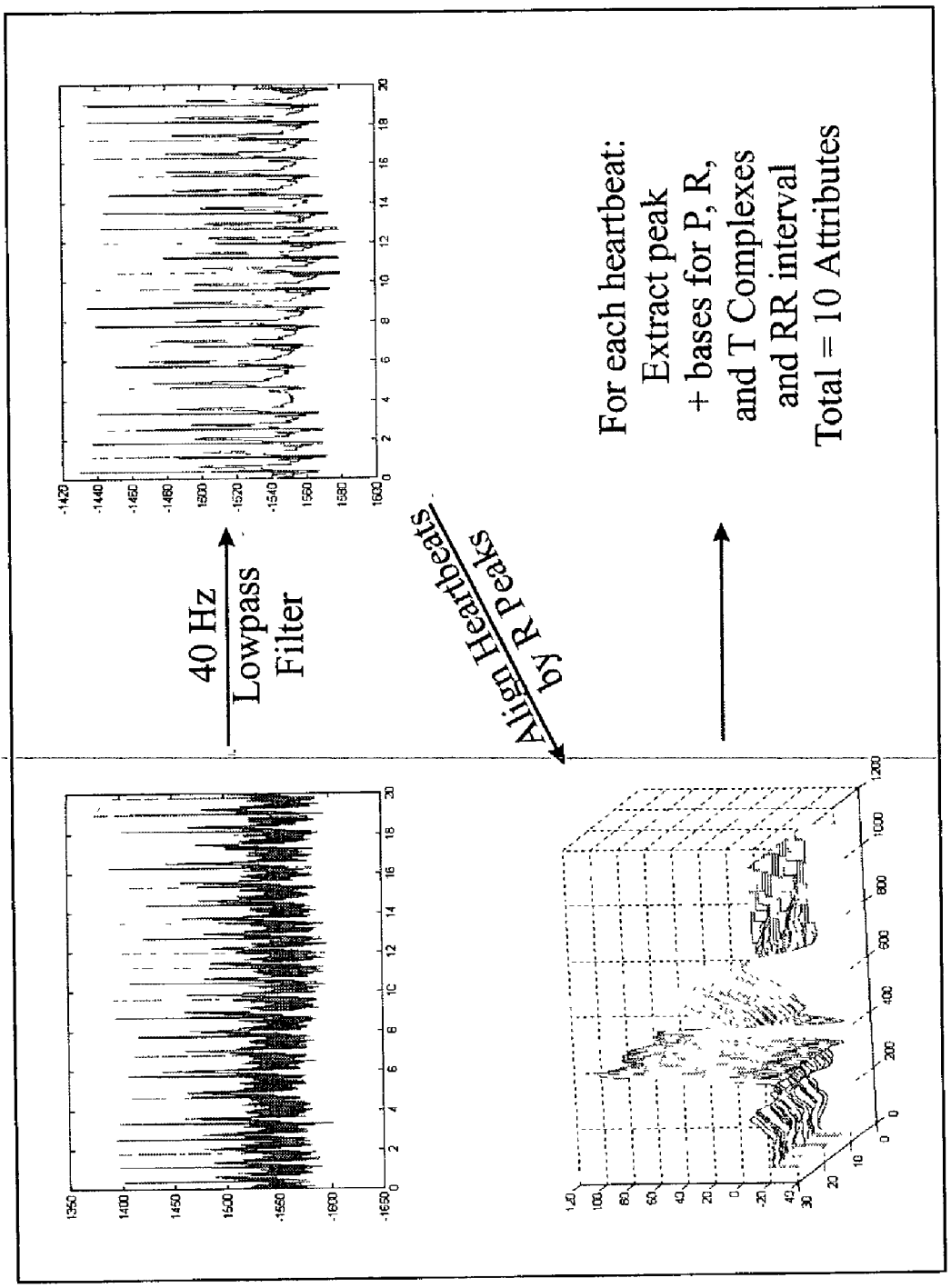
FIG. 3. Summary diagram of three basic data processing steps performed according to one embodiment of the invention.

To identify individuals based upon their ECG, some or all of several basic data processing steps may be performed. Illustrative steps are highlighted in FIG. 3. For example, the high frequency data may be filtered using a lowpass filter, such as a 40 Hz lowpass filter. The filter may be a hardware filter and/or a software filter, and may be configured to filter digital and/or analog information. The individual heartbeats may be aligned by, e.g., their R peaks, producing a waterfall diagram. Further, features may be extracted from the P, R, and/or T complexes for each heartbeat and/or the RR interval between heartbeats.

Sampling Frequency

The ECG may be sampled at a particular data collection rate. In some illustrative embodiments, the data collection rate may be higher than the standard data collection rate (which is about 200–250 samples per second). For example, the data collection rate may be approximately four times the standard data collection rate, or about 1000–1024, or 2000 or more samples per second. At this high data rate, the base positions of the P complex may be more easily separated from the Q position of the R complex and the start of the heartbeat.

Low Pass Filtering

Figure 4:
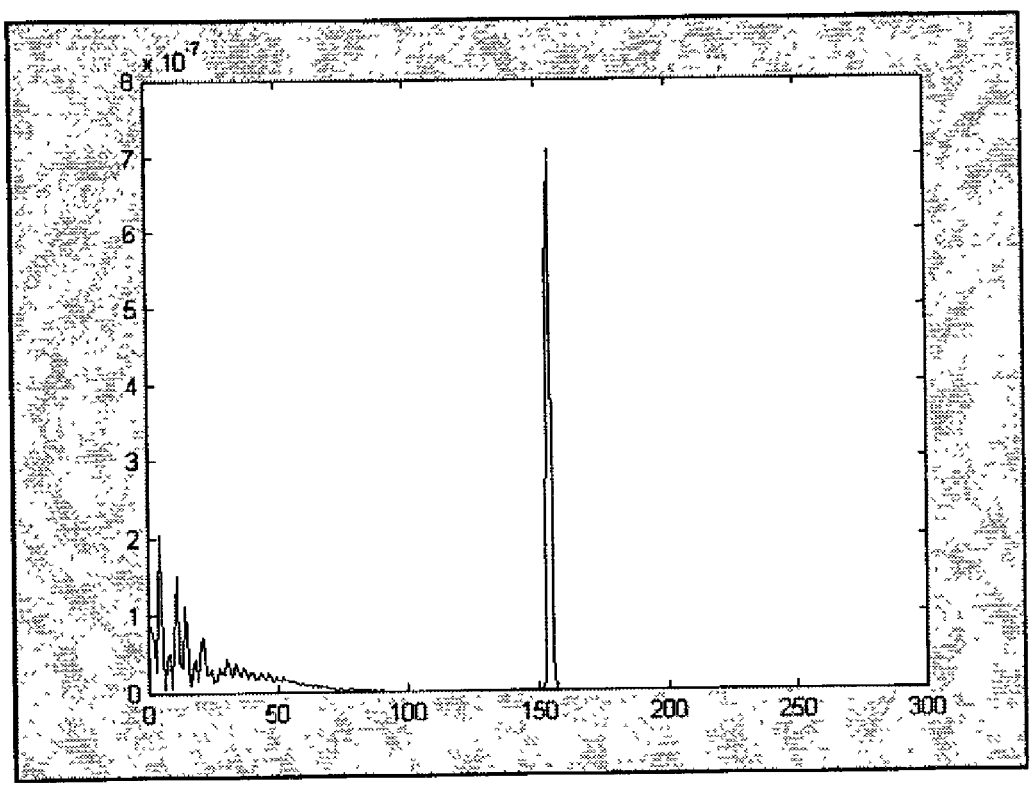
FIG. 4. Power spectral density of an electrocardiogram.

By observing ECG data across a range of subjects, we found the high frequencies are dominated by noise sources, particularly 60 Hz noise and its harmonics (FIG. 4). After several trials, we found a 40 Hz low pass filter eliminated most of the noise while retaining the attributes from the individual complexes. However, other lowpass filters having different passbands may be used. Fourier filtering may also be used to mitigate any problems associated with migration of edges.

Feature Extraction

Figure 5:
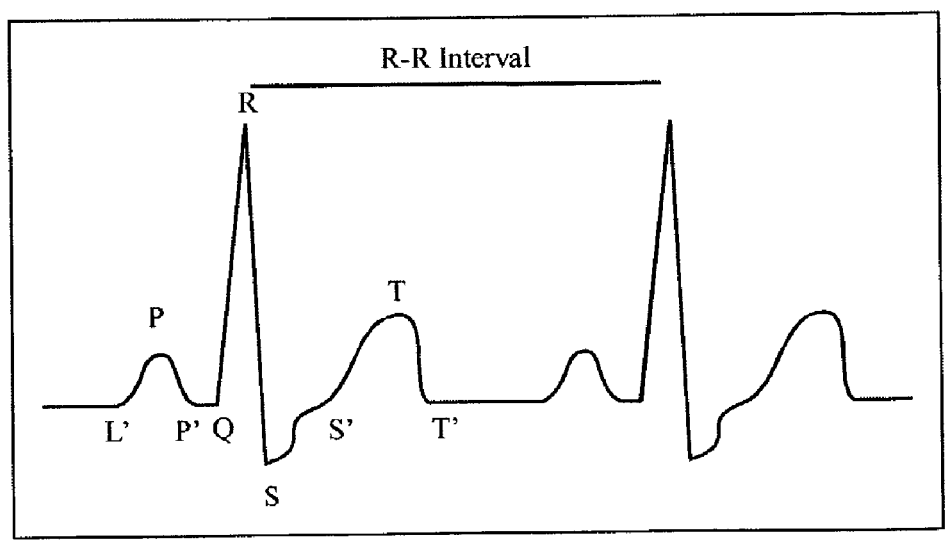
FIG. 5. Sample electrocardiogram, plotted as voltage vs. time, identifying the P, Q, R, S, and T portions of the heart beat.

The individual complexes that form the ECG for each heartbeat stem from different phenomenology. The attributes derived from the complexes contain sufficient information to characterize individuals. Examples of attributes that may be derived include the relative times for the peak and base positions of the individual heartbeat plus the RR intervals (FIG. 5). The times may be measured relative to the origin of the individual heartbeat and/or relative to the entire sequence of ECG information.

Individual attributes may be extracted using a variety of techniques. For instance, the R peak is in the region of maximum variance and high deviation from the heartbeat median. The R peaks define the origin of the heartbeat. The Q and S position may be found by trending the peak to its basis. The P complex may be obtained by repeating the process to the left of the R complex, while the T complex may be obtained by performing the analysis to the right of the R complex. The complex positions may then be normalized by the RR interval. The information may become robust if not invariant to state of anxiety. The data may be evaluated using one or more rules to filter undesirable data from the identification stage. An example of a such a rule is requiring that the T' position is smaller than the duration of the RR interval.

Pulse Oxymetry Data Processing

Figure 6:
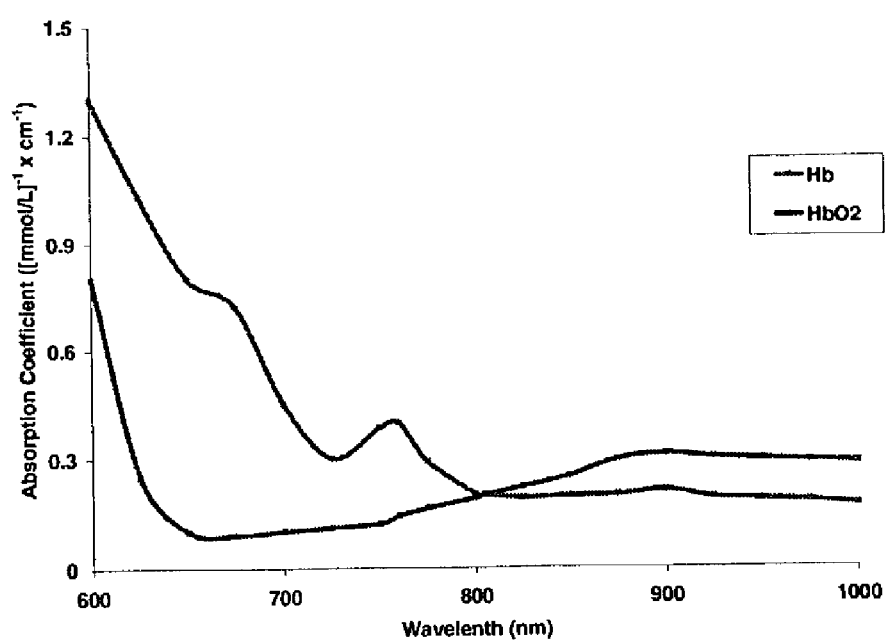
FIG. 6. Optical absorption coefficient for hemoglobin and deoxyhemoglobin.

Pulse oxymetry uses electro-optical sensing to quantify the level of oxygen in blood. The oxygen level cycles with each heartbeat, and sensors operating in the visible and near-infrared regions can be used to monitor this pattern of change (FIG. 6).

Video cameras with appropriate filters and processing can be used to collect datastreams on pulse oximetry in the 660 nanometer and 805 nanometer regions. The pulse oximeter signal can be reconstructed by synchronizing these two data streams.

Respiration Pattern Data Processing

Respiration information can be acquired by direct measurement of the temperature change associated with inhalation and exhalation near the nose and by a pressure transducer on the chest to measure changes associated with breathing and the expansion and contraction of the chest. Temperature changes associated with inhalation and exhalation are evident in thermal IR imagery. (FIG. 7). Infrared data may also contain information about biochemicals in the bloodstream or on the skin surface, which change with the respiratory cycle.

Criteria for Assessing Biometrics

A fundamental issue is the potential for each biometric to identify an individual. This question, however, can be couched in several ways. For example, given two sets of readings, we might ask if these are from the same individual. Another approach is to compare a new set of data to a series of observations that correspond to a registry of multiple individuals and ask if the new reading corresponds to a member of this registry. In either case, the analysis can be framed as a statistical test of hypothesis. The nature of the application would typically drive the acceptable level of type I and type II error in practice.

Various signal processing of biometric data may be used. Examples of such signal processing include noise filtering, signal decomposition, and/or feature extraction. It is envisioned that one, some, or all of the following attributes may be used in our classification/target recognition/data fusion algorithms, in any combination or subcombination: RR interval, width of the QRS complex, PQ time period, and the ST time period. The attributes may further be evaluated individually for frequency modulation, statistical distribution, and/or robustness to noise. Collectively, these attributes may be analyzed to determine their viability as biometrics.

Contact vs. Distance Sensing

Multiple sensing techniques may provide information about several phenomena related to the underlying physiological processes. For example, respiration may be measured in accordance with the mechanical activity and/or motion of the chest wall, and the thermal activity secondary to airflow at the nose (for example). Similarly, contact measurements of the heart rate and cardiovascular function may include the electrocardiogram (ECG), the cardiac output, and the pulse oximeter. The ECG may be used to provide a reference standard, while the heart rate cardiac output and pulse oximeter may be used in a manner analogous to standoff sensing using radar and electro-optical sensors. Table 2 shows an illustrative relationship among the contact and standoff sensing techniques.

TABLE 2

| Measurement | Contact/ Proximity Sensor | Distance Sensing Technique | Phenomenology |
| --- | --- | --- | --- |
| Respiration | Pressure Transducer | Laser vibrometer | Expansion/contraction of the chest (motion) |
|  |  | Radar |  |
|  | Thermal sensor | Longwave Infrared video imagery | Temperature changes with inhalation and exhalation (flow) |
| Heart rate variability | Cardiac Output (heart) | Radar | Mechanical movement of the heart |
|  | Pressure transducer (finger) | Laser vibrometer | Pulse (blood pressure) at carotid artery |
|  | Pulse oximeter | Pulse Oximetry | Oxygen levels associated with heart rate |

Basic physiological processes of interest may include, but are not limited to, one, some, or any of the following, in any combination or subcombination: the mechanical activity of the heart (which may include the motion of the valves and movement of the heart chambers), the pressure wave the skin surface associated with the pulse, and the change in blood oxygen levels and pressure associated with the pulse. A second approach is to measure the pressure wave associated with the pulse at some location on the body, such as the carotid artery, aorta or the radial artery. Laser vibrometry offers one method for performing this task at a distance. Unlike radar, however, laser vibrometry requires line-of-sight to the target area. A third approach, known as pulse oximetry, uses electro-optical sensing to quantify the level of oxygen in the blood. The oxygen level cycles with each heartbeat and sensors operating in the visible and near-infrared regions can be used to monitor this pattern of change.

In the contact data, respiration information may be acquired through various methods. For example, one may take a direct measurement of the temperature change associated with inhalation and exhalation near the nose. As another example, a pressure transducer may be placed on the chest to measure changes associated with breathing and/or the expansion and contraction of the chest. Any type of standoff sensor may be used, including radar, laser, and thermal imagery. Another approach, using a laser, may require a target area that moves with inhalation and exhalation. While clothing per se may not pose a-problem, loose clothing could attenuate the signal of interest. A third technique, which may prove the easiest approach operationally, is to collect thermal video data. Experiments have shown that the temperature changes associated with inhalation and exhalation is evident in thermal IR imagery (FIG. 7). Infrared data may also contain information about biochemicals in the bloodstream or on the skin surface, which change with the respiratory cycle.

Figure 26:
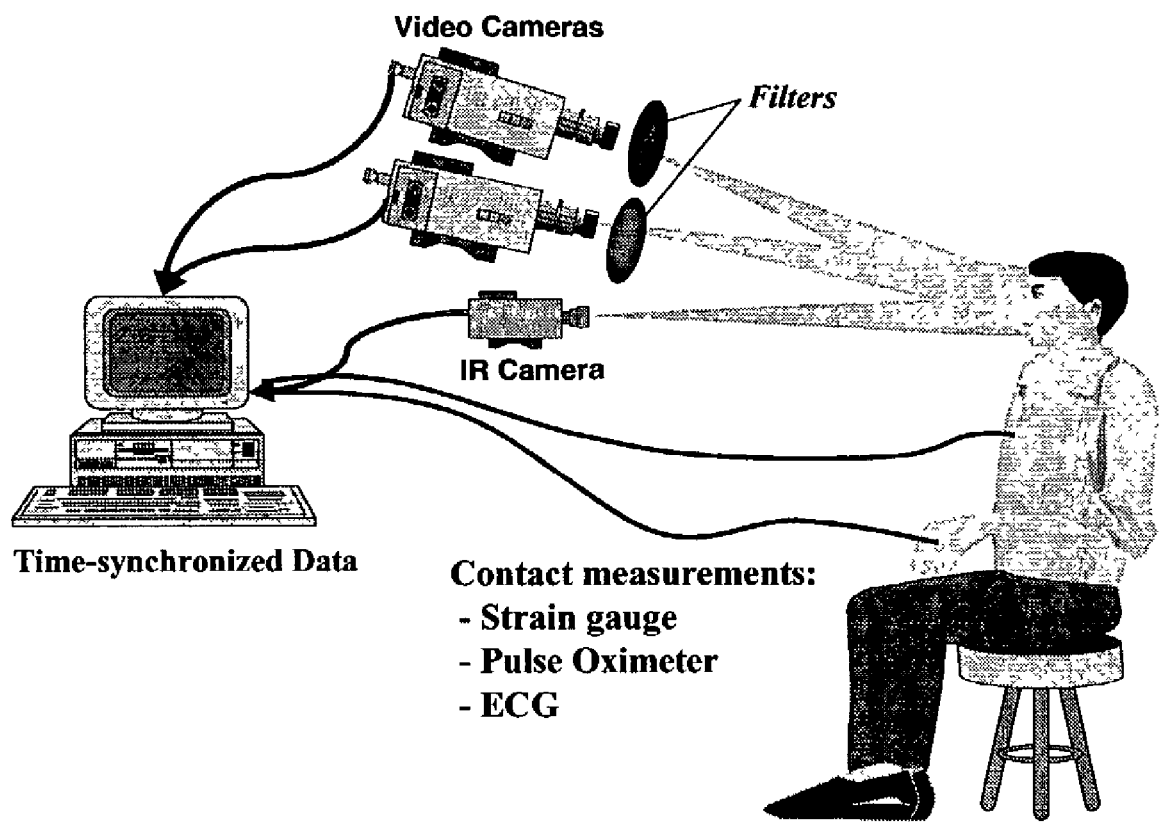
FIG. 26. Example of a data collection scheme.

One illustrative strategy is to use a plurality of sensors, such as three video cameras, with appropriate filters and processing, to collect datastreams on respiration and/or pulse oximetry (FIG. 26). A first sensor may be a thermal video sensor that provides standoff data on respiration. Two other sensors may be two digital video cameras, with appropriate filters, that collect data in the at two different wavelength regions, such as at 660 nanometer and 805 nanometer regions. By synchronizing these two data streams, the pulse oximeter signal can be reconstructed.

Compilation of a Database

Figure 25:
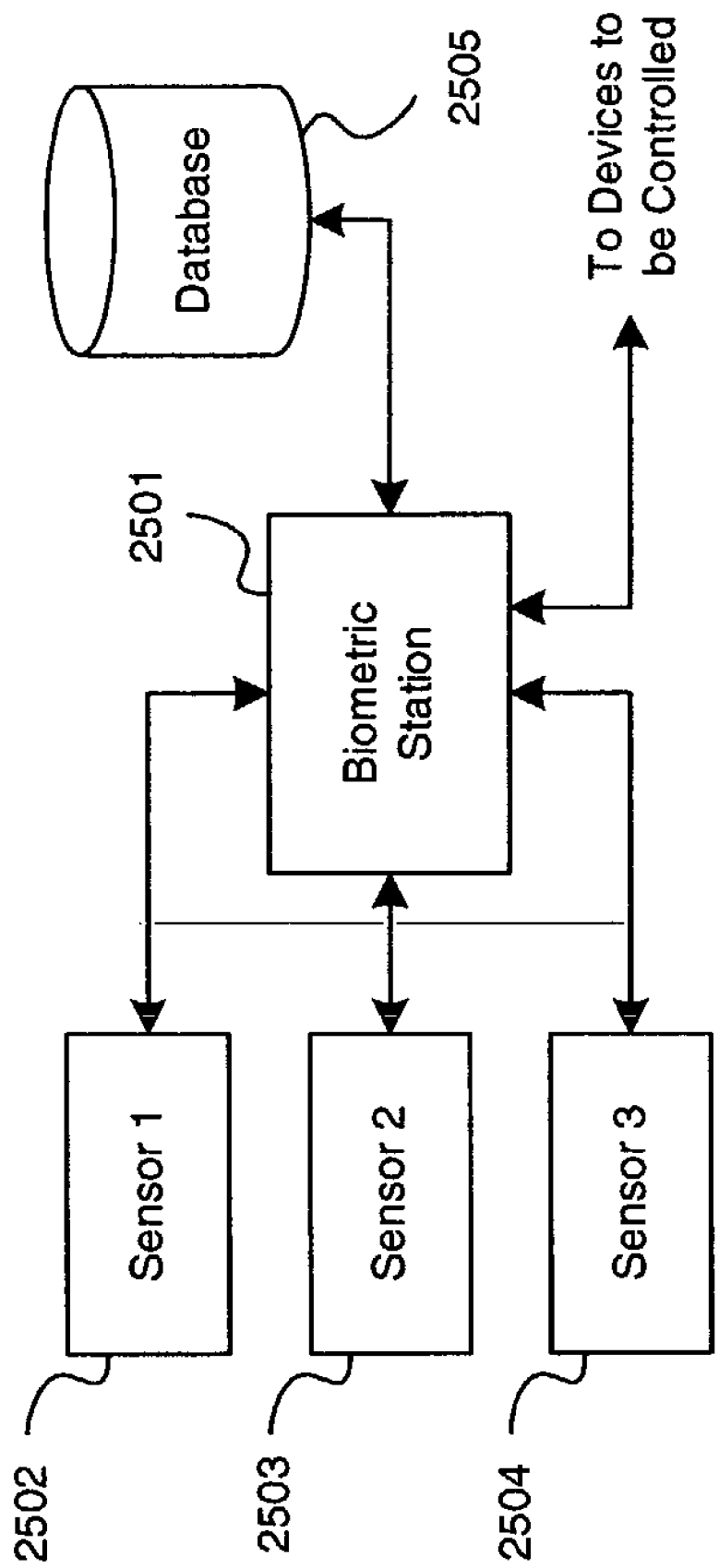
FIG. 25. Functional block diagram of an illustrative embodiment of a biometric measurement system in accordance with aspects of the present invention.

A set of biometric data for a plurality of individual subjects may be measured and stored as a collection of biometric data. For each subject, the biometric data may include some or all of the biometric data discussed herein using any method such as any of the techniques discussed herein. The data collection may be stored in any one or more storage devices such as a database 2505 (FIG. 25). The storage device(s) may be embodied as one or more hard drives, disk drives, memory, tape drives, and/or the like. In the data collection, the biometric data for each subject may be uniquely associated with an identity of the respective subject, and/or associated with a group of subjects. The identity may be a name of the subject, a serial number of the subject, and/or any other identifying information that may uniquely identify the individual subject and/or group of subjects.

Identification of Subjects

Once a data collection is established, the biometric data for a subject in the data collection may be compared with the biometric data in the data collection for some or all of the subjects included in the data collection. This comparison may yield information that can help identify a subject as someone who is already included in the data collection.

Referring to the illustrative system of FIG. 25, the data collection, which may be embodied as the database 2505, may be coupled to a biometric station 2501. The biometric station 2501 may be any type of device or system that can access the biometric data from the database, such as a computer, a laptop computer, a personal computer, a mainframe computer system, a personal digital assistant, a palmtop computer, and/or the like. The biometric station 2501 may further be incorporated into any other device or appliance, such as a cellular phone, vehicle, portable biometric identification device, and the like. The biometric station 2501 may further be coupled to one or more biometric sensors 2502, 2503, 2504 of any type such as the type discussed herein. The biometric sensors 2502–2504 may be wired, wireless, internal to the subject's body, external to the subject's body, and/or a standoff-type sensor. The biometric station 2501 may further be coupled to one or more devices and/or appliances to be controlled in accordance with a comparison of data from the biometric sensors 2502–2504 and the data in the database 2035. The biometric station 2501 may be configured in accordance with particular hardware and/or software to process biometric data and compare biometric data. For example, the biometric station 2501 may be configured to implement data filters, correlation functions, estimation functions, normalizing functions, and/or the like.

In operation, the biometric sensors 2502–2504 in the illustrative embodiment may obtain raw biometric data from a first subject in accordance with the aspects of the invention described herein. The raw biometric data may be processed and/or analyzed to generate processed biometric data for the first subject using any or all of the techniques discussed herein. The database 2505 may contain raw and/or processed biometric data for one or more subjects such as a second subject and a third subject. The processed biometric data for the first subject may be compared with the biometric data for the second and/or third subjects. Based on a comparison, an output interface such as a display screen, a voice generation system, and/or the like (which may be part of the biometric station 2501) may output a result. The biometric station 2501 may further send one or more control signals to one or more devices and/or appliances in accordance with the comparison. For instance, where the processed biometric data for the first subject matches exactly, or within a predetermined threshold error range, the biometric data in the database 2505 for the second subject, the biometric station 2501 may determine that the first subject is the same subject as the second subject. Or, where there is not a match, the biometric station 2501 may determine that the first subject is not the same subject as the second subject. The biometric station 2501 may send the control signals to the devices and/or appliances to be controlled based on a number of factors such as whether there is a match and/or with which subject in the database 2505 the first subject's biometric data matches. Examples of devices or appliances to be controlled may include a vehicle, a cellular phone, a door to a building and/or anything else that one may desire to secure through biometric identification and/or confirmation.

All patents, patent applications, and references cited in this disclosure are incorporated herein by reference in their entirety. The following examples are provided to illustrate various aspects of the invention and do not limit the invention, which is described by the appended claims.

EXAMPLE 1

Overview of the Collection of Specific Physiological Data

Figure 8:
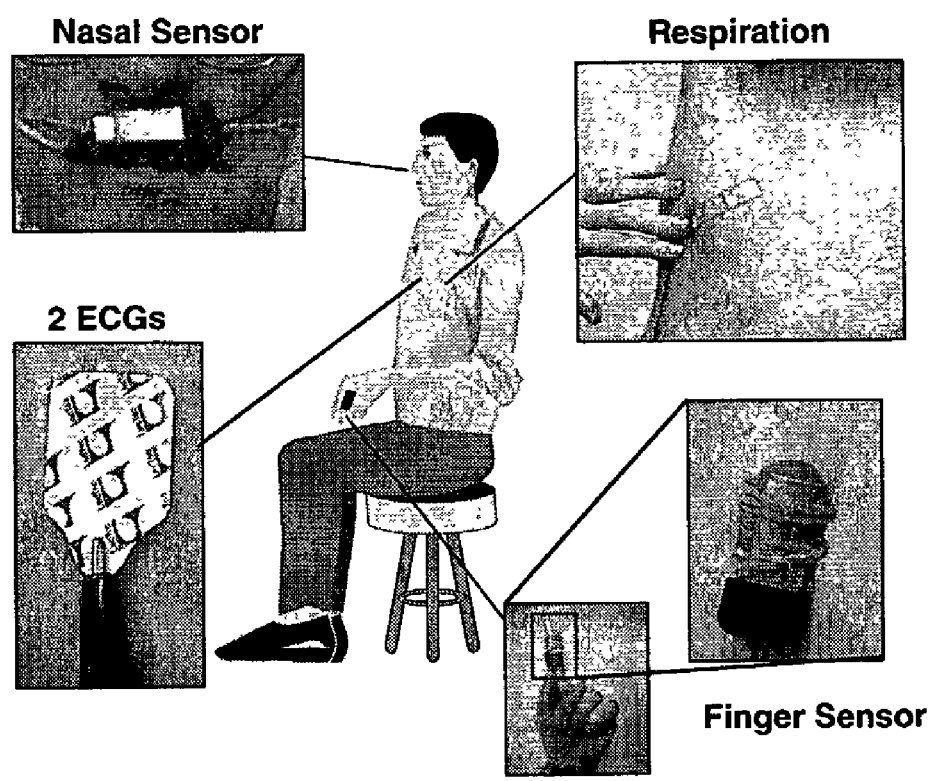
FIG. 8. Example of a data collection scheme for simultaneous measurement of ECG, pulse oximetry, chest expansion, and breath temperature.

The core of this set of illustrative experiments is the collection of specific physiological data to address non-imaging biometrics. In this example, the core experiment focused on the collection of heart rate, respiration, and body resonance data from several contact and close proximity sensors (FIG. 8). Subjects performed a variety of tasks designed to stimulate various mental and emotional responses that could alter the observed physiological processes. Because the goal of this research was to develop signatures for human identification, it was imperative in this example that these new biometrics perform well across a range of conditions. The data collected in this experiment provided the information needed to test robustness across mental and emotional states.

It is well known that heart rate and respiration can vary with a person's mental and emotional state. To measure this variability and assess its effect on human identification, we developed a strict protocol in which the subject performs a series of tasks. These tasks range from a relaxed, meditative state to tasks likely to induce varying levels of concentration and stress. Preliminary measurements indicated that heart rate and respiration vary across these tasks. Measurements were collected during these tasks and during the recovery, period as well. All measurements were collected by trained psychology professionals under strict procedures to insure high quality, consistent data.

Ancillary experiments included infrared (IR) video imagery and body resonance measurements. IR video can monitor the change in temperature around the nose and mouth associated with respiration. The core experiment collected strain-gauge data on respiration and temperature measurements close to the nose. In a separate experiment, we confirmed that robust respiration data can be collected remotely, using an IR sensor. The core body resonance experiment collected data when the subject was speaking.

EXAMPLE 2

Sensors for Data Collection

In this example, a set of sensors was identified to collect contact biometrics data, as shown in Table 3.

TABLE 3

Sensors and Associated Biometric Measurements

| Biometric | Measurement | Sensor |
|---|---|---|
| Heart Rate | Electrical activity | ECG |
| Variability | Heart beat | Pressure transducer |
|  | Pulse | Piezoelectric transducer |
| Respiration | Nasal temperature change | Thermal sensor |
|  | Chest movement | Pressure transducer |
| Body Resonance | Recorded speech | Microphone |
| Face Recognition | Imagery | Video camera |

Where possible, multiple sensors collected data related to the same underlying physiological process. For example, information about respiration was collected using a thermal sensor at the nose to measure the air temperature changes associated with inhalation and exhalation. At the same time, a strain gauge measured the expansion and contraction of the chest associated with respiration. The full suite of sensors was integrated into a single laboratory system, so that data were collected simultaneously and were temporally registered to a single system clock.

Temperature Probe (LDT1-028Kpiezoelectric Transducer)

This non-contact probe can be used to collect changes in temperature in the immediate vicinity of the subject's nose. It can be used as a surrogate for an IR camera. This probe has a piezoelectric response coefficient of 16 mV/K and a piezoelectric charge coefficient of 30 mV/m2 K.

Contact Microphones (CPS4P Contact Microphone)

These contact microphones can be used as surrogates for a laser vibrometer. The microphones can be used in a two microphone configuration or in a one microphone/one speaker configuration. The two microphone configuration requires that one microphone be placed at the larynx to record the driving signal. The second microphone is placed at over a resonance cavity, to record the response to the driving signal. The one microphone configuration replaces the driving signal from the larynx with a driving signal from an external speaker. The driving signal is a swept frequency signal ranging from 2 Hz to 30 kHz. The microphone is placed over a resonance cavity to record the response. The microphones have a flat frequency response from 2 Hz to 50 kHz, with less than a 3 dB variation over this range.

Pressure Transducers (LDT2-028K LDT2-052K LDT4-028K)

These probes can be used to collect simultaneous multiple-site heart and respiration biometrics and used to record surface measurements.

TABLE 4

Comparison of piezoelectric materials

| Property | Units | PVDF Film | PZT | BaTiO$_3$ |
|---|---|---|---|---|
| Density | $10^3$ kg/m3 | 1.78 | 7.5 | 5.7 |
| Relative Permittivity | $\epsilon/\epsilon_0$ | 12 | 1,200 | 1,700 |
| $d_{31}$ Constant | $(10^{-12})$ C/N | 23 | 110 | 78 |
| $g_{31}$ Constant | $(10^{-3})$ Vm/N | 216 | 10 | 5 |
| $k_{31}$ Constant | % at 1 kHz | 12 | 30 | 21 |
| Acoustic Impedance | $(10^6)$ kg/m$^2$-sec. | 2.7 | 30 | 30 |

Figure 9:
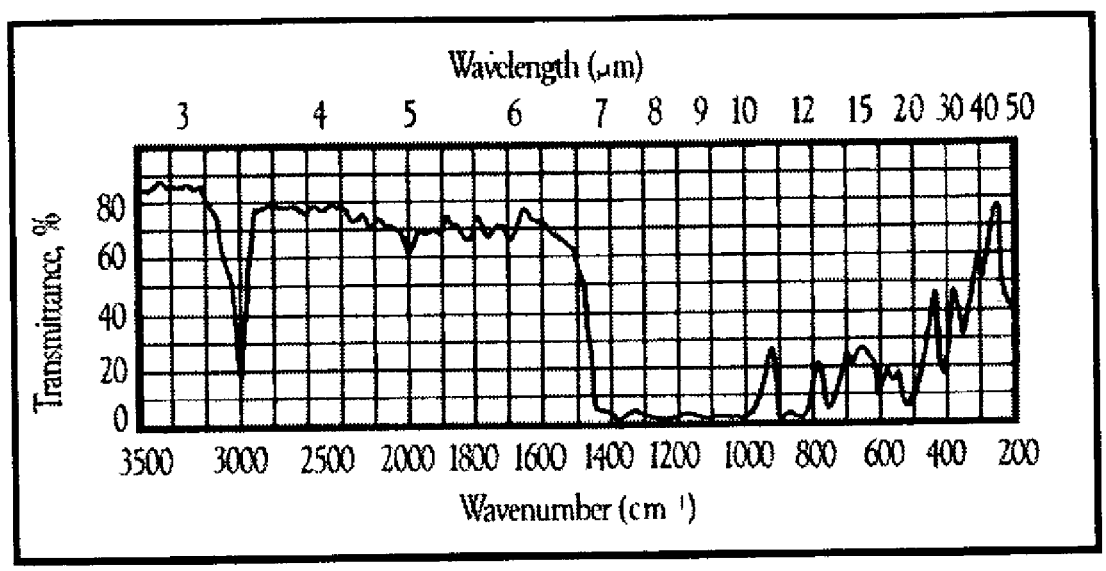
FIG. 9. Example of an infrared absorption spectrum of PVDF film.

A typical infrared absorption spectrum of PVDF film is shown in FIG. 9.

TABLE 5

Typical properties of piezo materials

| Symbol | Parameter | PVDF | Copolymer | Units |
|---|---|---|---|---|
| t | Thickness | 9, 28, 52, 110 | Various | $\mu m$ (micron, $10^{-6}$) |
| $d_{31}$ | Piezo Strain Constant | 23 | 11 | $10^{13} \frac{m/m}{V/m}$ or $\frac{C/m^2}{N/m^2}$ |
| $d_{33}$ |  | −33 | −38 |  |
| $g_{31}$ | Piezo Stress constant | 216 | 162 | $10^3 \frac{V/m}{N/m^2}$ or $\frac{m/m}{C/m^2}$ |
| $g_{33}$ |  | −330 | −542 |  |
| $k_{31}$ | Electromechanical | 12% | 20% |  |
| $k_3$ | Coupling Factor | 14% | 25–29% |  |
| C | Capacitance | 380 for 28 $\mu m$ | 68 for 100 $\mu m$ | $pF/cm^2$ @ 1 kHz |
| Y | Young's Modulus | 2–4 | 3–5 | $10^9 N/m^2$ |
| $V_0$ | Speed of Sound |  |  |  |
|  | stretch: | 1.5 | 2.3 | $10^3$ m/s |
|  | thickness: | 2.2 | 2.4 |  |
| p | Pyroelectric Coecfficient | 30 | 40 | $10^6 C/m^2 \degree K.$ |
| $\epsilon$ | Permittivity | 106–113 | 65–75 | $10^{12}$ F/m |
| $\epsilon/\epsilon_0$ | Relative Permittivity | 12–13 | 7–8 |  |
| $\rho_m$ | Mass Density | 1.78 | 1.82 | $10^3$ kg/m |
| $\rho_e$ | Volume Resistivity | >$10^{13}$ | >$10^{14}$ | Ohm meters |
| $R_\square$ | Surface Metallization | 2.0 | 2.0 | Ohms/square for CuNi |
| $R_\square$ | Resistivity | 0.1 | 0.1 | Ohms/square for Ag Ink |
| tan $\delta_e$ | Loss Tangent | 0.02 | 0.015 | @ 1 kHz |
|  | Yield Strength | 45–55 | 20–30 | $10^6 N/m^2$ (stretch axis) |
|  | Temperature Range | −40 to 80 | −40 to 115 . . . 145 | $\degree$ C. |
|  | Water Absorption | <0.02 | <0.02 | % $H_2O$ |
|  | Maximum Operating Voltage | 750 (30) | 750 (30) | V/mil(V/$\mu m$), DC, @ 25$\degree$ C. |
|  | Breakdown Voltage | 2000 (80) | 2000 (80) | V/mil(V/$\mu m$), DC, @ 25$\degree$ C. |

ECG Electrodes (AV303)

In this particular example, standard ECG electrodes were used to collect truth data of electrical heart activity for correlation with other biometric signatures. Each of the contact and close proximity devices produces an output voltage. The voltages from all devices were acquired using a single analog-to-digital conversion unit. The digital output was in the form of sixteen bit integers. These values were then scaled based upon the amplifier's bias. This enables synchronization among devices. The data was then stored in a single ASCII datafile.

EXAMPLE 3

Tasks and Conditions for Subjects

In this next example, a commonly used stress-inducing protocol was administered to the subjects to evaluate the effect of various physiological conditions on biometric parameters. In general, there are four stages of mental condition that can be evaluated in the lab: baseline phase, meditative phase, stressor stages, and recovery stages. Seven different two-minute tasks were given to participants to measure these stages. Participants initially had physiological parameters monitored and recorded while in a relaxed, but not meditative, condition. Next, participants were asked to relax as fully as possible with eyes remaining open and room lights dimmed. Next, they were asked to read non-provocative material (Declaration of Independence) and then perform simple mathematical tasks (serial 7's). Following these two procedures, they were allowed to recover to allow physiological signals to return to near baseline levels. After this initial recovery period, they then participated in a simulated driving task where a variety of stressors were sequentially added, making the driving task progressively more difficult. Following this stressor exposure, they were allowed to relax, and data was obtained during the final recovery phase.

Participants then performed four 30-second readings of the Gettysburg Address while acoustic data was measured at four different sites: sternum, behind left ear on the mastoid, on the left maxillary sinus, and on the back over left lower lung. Acoustic data also was collected over the left larynx for all four readings.

EXAMPLE 4

Experimental Procedures

In this example, sensors were placed on participants in the following order:

1. To measure breathing, a long piezoelectric sensor was situated along the side of the torso, opposite to the participant's handedness (i.e., left side if right handed and visa versa) mid-clavicular line of the tenth rib, toward the anterior mid-axillary line. This sensor was secured with an elasticized Ace bandage that was wrapped tightly around the participant's torso. The Ace bandage fit snugly but did not cause discomfort or inhibit breathing. This lead was connected to Port 2 of an analog to digital converter for data collection (see Example 5).

2. A second breathing measure was obtained by placing a piezoelectric sensor beneath the participant's nose. As this sensor reacts to temperature change, it was kept slightly elevated from the heat of the participant's skin by resting on a hollow plastic tube placed on the upper lip. The plastic tube was held in position under the nose by an elasticized band that fits around the participant's head, fitting above the ears. Both the sensor and plastic tubing were thoroughly cleansed with alcohol prior to being placed on the participant. The alcohol was allowed to evaporate before the sensor was placed on the participant. This lead was connected to Port 4 for data collection.

3. Two leads were used to measure heart activity. The first was attached to electrodes positioned on the upper right anterior chest and the left hypogastric area. This lead was connected to Port 0 for data collection. The second lead was attached to electrodes positioned on the upper left anterior chest and the right anterior neck triangle. This lead was connected to Port 5 for data collection. In both cases, positive leads were placed inferior to negative leads. Standard commercially available ECG electrodes that come pre-packaged with adhesive gel were used. The wire leads were attached to the specific electrode attachment site on the ECG electrodes.

4. A short piezoelectric sensor was used to measure heart activity and breathing simultaneously. Placement for this sensor was determined by locating the Point of Maximal Inpulse (PMI) of the heart, approximated by the mid-clavicular line (MCL) and the fifth intercostal space (ICS) on the left side. This sensor was attached to the participant's torso with the use of double-sided tape, and the lead wire was secured using surgical tape. The location of the PMI was facilitated by using a stethoscope to locate the position where the heart sounds are clearly heard. Lung sounds can also be identified with the use of the stethoscope. This lead was connected to Port 1 for data collection.

5. One long piezoelectric sensor was wrapped around the index finger tip of the participant's non-dominant hand and held in place by an elasticized band. The elasticized band was tightened so that the participant felt a "gentle throb" sensation in their fingertip. The participant was instructed to inform the research associate if any discomfort developed while wearing the elastic band. This lead was connected to Port 3 for data collection.

6. A Nellcor N-1000 unit is used to measure end tidal carbon dioxide ($ETCO_2$) and pulse oximetry. The participant was fitted with a #4706-F cannula from Salter Labs and wore a sensor on the middle finger of the non-dominant hand. The $ETCO_2$ was measured in Port 6, and the pulse oximetry data was collected in Port 7.

As each sensor was secured, in the present example, a 15 second signal reading was taken to assess the signal to noise ratio obtained by the sensor, insuring that clear physiological signals without interference, impedance, or extraneous artifacts were present. During this brief reading, the participant was asked to sit quietly without talking. Any necessary adjustments to improve the quality of the signal readings were made immediately.

Once all sensors provided adequate signal readings, the participant was directed to look directly at the camera for approximately 5 seconds, so that an image of the sensor placement could be recorded. Before beginning the recording, the camera angle was adjusted to the participant's height and body position.

Data were collected continuously according to an exact protocol defined in an informed consent form. The baseline, eyes open meditation, reading task, arithmetic task, initial recovery, driving task, and final recovery phase data were recorded. The following time sequence was followed:

TABLE 6

Time sequence of data to be collected in Example 4

| Task | Protocol | Time |
| --- | --- | --- |
| Task 01 | Initial Baseline | 2 minutes |
| Task 02 | Eyes Open Meditation | 2 minutes |
| Task 03 | Reading Task | 2 minutes |
| Task 04 | Arithmetic Task | 2 minutes |
| Task 05 | Initial Recovery | 2 minutes |
| Task 06 | Driving Task | 2 minutes |
| Task 07 | Final Recovery | 2 minutes |

All leads were removed from the participant so that acoustic data could be collected in the following time sequence:

TABLE 7

Time sequence of acoustic data to be collected in Example 4

| Task | Protocol | Time |
| --- | --- | --- |
| Task 08 | Reading Task | 30 seconds |
| Task 09 | Reading Task | 30 seconds |
| Task 10 | Reading Task | 30 seconds |
| Task 11 | Reading Task | 30 seconds |

For Tasks 8–11, one acoustic sensor was placed on the left larynx, and data was collected in Port 6. A second acoustic sensor, in Port 7, was attached to four different sites for the four tasks in the following order: sternum, behind left ear on left mastoid, over left maxillary sinus, and on back over left lower lung area.

With the camera still in the record mode, data collection procedures began as follows:

1. First, the participant was asked to sit quietly for 2 minutes to obtain a baseline physiology recording. During this recording, the computer screen in front of the participant was turned off, and the participant was directed to refrain from talking.

2. Once the baseline measure had been recorded, the overhead lights were extinguished and replaced by the softer light of a desk lamp. In addition, soft relaxation music was played. The participant was directed to become as relaxed as possible, keeping the eyes open for this 2-minute recording.

3. Upon completion of the meditative/relaxation period, overhead lighting was restored and the music was stopped. A printed copy of the Declaration of Independence was placed on a stand in front of the participant, at a distance appropriate for reading. The participant was instructed to read the Declaration "out loud, in a normal speaking voice tone." He or she was further instructed to continue reading until directed to stop (2 minutes). Once told to stop reading, the Declaration was removed from the participant's view.

4. For the next task, the participant was asked to count backwards by 7's, beginning with the number 1,014, and to continue counting until instructed to stop. The participant was told to go as quickly as possible but to try and avoid making mistakes. The participant was told that if a mistake in subtraction is made, it will be corrected and the participant would be directed to resume counting from the last correct number verbalized. Once the participant began counting, errors were corrected by the researcher stating in a neutral tone, "begin with _____ (the last correct #)." The participant was instructed to stop counting after 2 minutes.

5. For the next two minutes, the participant was asked to sit quietly so that a measure of recovery from the above stressors could be obtained.
6. Next, the computer screen in front of the participant and the speakers was turned on and s/he was positioned at a comfortable reaching distance from the driving steering wheel. The participant was instructed to drive through a "virtual city" at a fast pace "as if you are racing. You don't have to follow the rules of the road or any particular path. Just try to avoid crashing your car." In addition the participant was directed to use only the dominant hand to operate the steering wheel and to use the foot pedals to activate the motion of the car. The participant's non-dominant hand was placed in a resting position on the arm of the chair. After 2 minutes, the driving simulator, along with the speakers and computer screen, was turned off.
7. For the next two minutes, the participant was instructed to sit quietly while the recovery rate of their physiology was measured.

Figure 10:
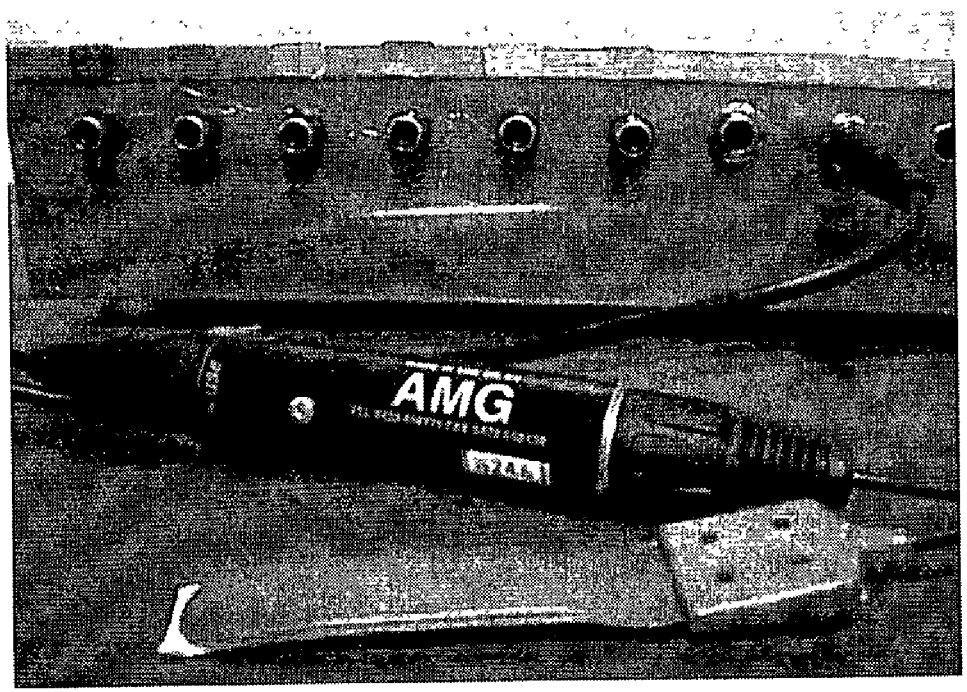
FIG. 10. Example of two acoustic sensors that can connect to the data ports for digital data collection.

Following completion of this task, the sensors were removed from the participant so that acoustic sensors can be attached and acoustic data collected (FIG. 10). Data collection was as follows:

8. For 30 seconds, the participant read the Gettysburg Address while acoustic data was collected with two acoustic sensors placed over the left larynx (Port 6) and sternum (Port 7).
9. For 30 seconds, the participant read the Gettysburg Address while acoustic data was collected with two acoustic sensors placed over the left larynx (Port 6) and behind the left ear over the left mastoid (Port 7).
10. For 30 seconds, the participant read the Gettysburg Address while acoustic data was collected with two acoustic sensors placed over the left larynx (Port 6) and over the left maxillary sinus (Port 7).
11. For 30 seconds, the participant read the Gettysburg Address while acoustic data was collected with two acoustic sensors placed over the left larynx (Port 6) and on the back over the lower left lung area (Port 7).

Following completion of this final task, the camera recording was stopped, and the acoustic sensors were carefully removed. Any discomfort experienced by the participants was carefully documented on the protocol form under the heading titled "adverse effects." If no adverse effects were experienced, the "none" box was checked.

The following meta data were then collected for the participant's session:
1. Time
2. Date
3. Race/Ethnicity
4. Age
5. Gender
6. Time of last alcohol consumption
7. Time of last caffeine consumption
8. Time of last nicotine usage
9. Time of last medication usage
10. Time of last illicit drug usage
11. Time of last meal
12. Any medical conditions
13. General state of health
14. Hours of sleep for previous night
15. Height
16. Weight At this time, participants were allowed to ask any additional questions and then underwent a short debriefing at which time contact information of the principal investigator was made available should any further questions or issues arise following the study. In addition, participants who were willing to undergo further evaluation and repeat testing were placed into a confidential database that was kept in a secure location for further inquiries.

EXAMPLE 5

Data Capture

In this example, we collected contact ECG data and indirect heart rate data at 200 or greater Hz. The breath rate data at the nose and chest were also collected at 200 or greater Hz. These four measurements were stored in a single text file. A total of 16 fields was stored, as each measurement was collected with a time stamp. The individual measurements were offset by some minimal time increment, as a single analog-to-digital converter operated on the entire datastream. Each session was recorded using a digital NTSC VHS system. From these, individual still frames were recorded in image bitmap format. The still frames were used for matching data to information as required for privacy protocols.

In a separate test stream, a portion of the subjects were evaluated for body resonance. Acoustic signals were acquired from 3 or 4 positions on the body. The individual recordings was stored as separate wave files. A wave file is a common digital binary data format for speech processing.

Data was collected concurrently on up to 8 differential channels using a Keithley 3108 analog to digital converter. The signals were digitized to 16-bit accuracy. Biometric channels were with at a 1 kHz refresh rate. The time delay between channels was 0.1 milliseconds. Channel 0 through 5 were buffered with an RC filter with a time constant of 1 millisecond.

During tasks 1 through 7, Channels 6 and 7 collected the pulse oximetry and $CO_2$ measurements. For tasks 8 through 11, Channels 6 and 7 collected acoustic signals at 22.010 kHz. The time delay between channels was 0.1 milliseconds.

TABLE 8

Data Port and Sensor Configuration for Example 5

| Port No. | Tasks | Sensor Type | Measurement |
|---|---|---|---|
| Heart and Respiration Phase | | | |
| 0 | 1–7 | ECG | Heart Rate Variability |
| 1 | 1–7 | Pressure Transducer | Respiration and heartbeat |
| 2 | 1–7 | Pressure Transducer | Respiration (chest) |
| 3 | 1–7 | Pressure Transducer | Pulse in finger |
| 4 | 1–7 | Temperature | Respiration (nares) |
| 5 | 1–7 | ECG | Heart Rate Variability |
| 6 | 1–7 | $CO_2$ | $ETCO_2$ |
| 7 | 1–7 | Pulse Oximeter | Pulse Oximetry |
| Body Resonance Phase | | | |
| 6 | 8–11 | Microphone | Body resonance (laryngeal contact) |
| 7 | 8–11 | Microphone | Body Resonance (various sites) |

EXAMPLE 6

Data Analysis

In this example, we constructed a family of ROC curves that show performance for each biometric individually within a single task, for individual biometrics operating across tasks, and for fusion of the biometrics. The analysis proceeded through several phases:
1. Data Quality. An initial screening identified any anomalies, outliers, or other issues that could affect the integrity of the data for subsequent analysis.
2. Feature Extraction. A variety of exploratory data analysis tools was employed to extract features from the temporal data that could form the basis for human identification
3. Feature Assessment. This phase characterized the statistical behavior of the relevant features. This analysis quantified within- and between-subject variability, both within each task and across tasks, to assess the stability of features across a range of mental and emotional states. Further investigation explored the independence and possible interactions among the features.
4. Separability. Because the ultimate objective was the development of biometric techniques for identifying individuals, the next step was the construction of functions of selected features that could serve as unique identifiers for individuals. The separability among individuals is an indicator of the viability of these biometrics.
5. Classification Analysis This stage of the analysis employed the preceding results to propose concepts for operational biometric algorithms. Specific classification methods were applied to the extracted features to identify specific individuals. Biometrics were analyzed separately to assess each one. Then a merged classifier pooled information across biometrics to quantify the performance improvement attributable to fusion of the biometrics.

Analytic Issues for Individual Non-imaging Biometrics

The following analytic issues for individual non-imaging biometrics were considered in Example 5:
1. Do the individual modalities contain sufficient information to allow target identification?
2. Is the feature space distance between two individuals for a given modality larger than the intra-subject variability?
3. How does the emotional and mental state of the subject affect separability among individuals?
4. How are the data distributed in each modality?
5. Is the distribution of the data consistent between individuals?
6. Can we uniquely characterize the emotional and mental state of the individual?
7. What are the noise sources for each modality?
8. How do these noise source affect separability among subjects?

Analytic Issues for Combining Multiple Modalities

The following issues were considered with respect to combining multiple modalities:
1. Characterization of the contribution from the individual modalities
2. Does the fusion of the multiple modalities considerably improve classification performance?
3. Can we quantify the improvement that an additional modality will have on the system performance?

EXAMPLE 7

Data Analysis and Feature Identification

Figure 11A:
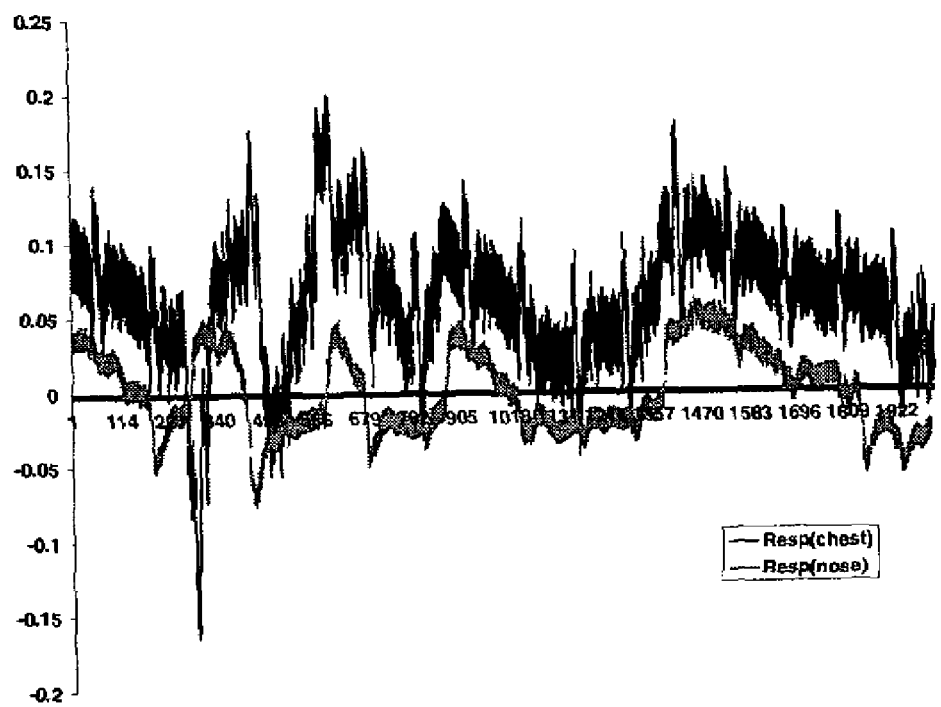
FIG. 11A, raw data for two sensors measuring respiration exhibit the 60 Hz noise.
Figure 11B:
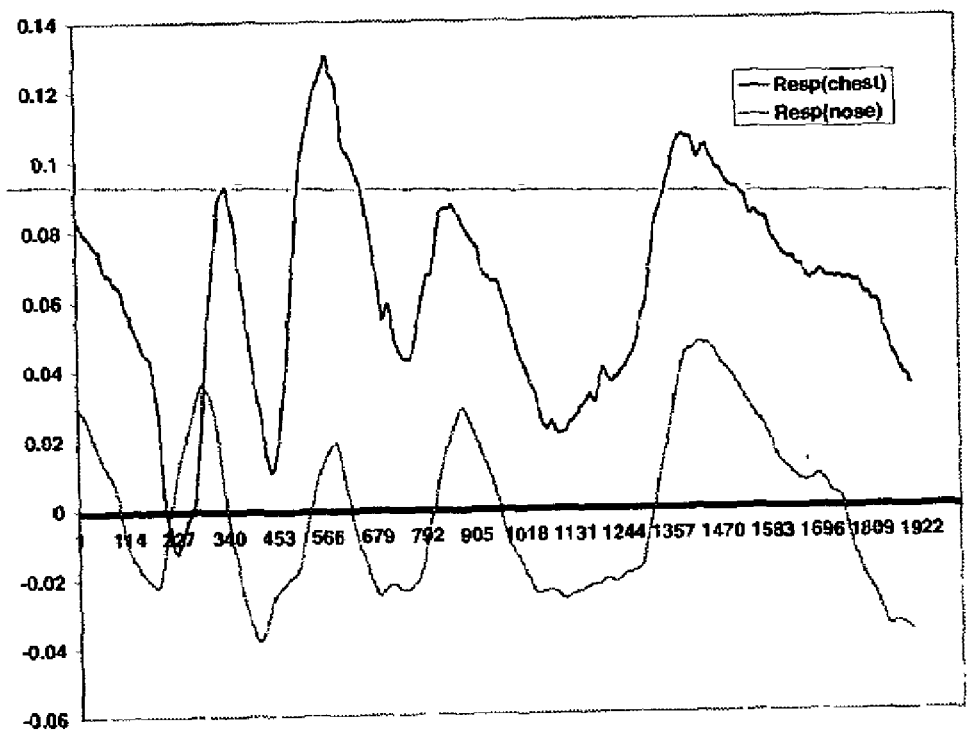
FIG. 11B, processed data for two sensors measuring respiration with the 60 Hz noise removed.

In this example, the data analysis began with an assessment of data quality. Any outliers or anomalous measurements were flagged and investigated. In addition, sources of noise were explored and, where possible, quantified. The statistical tools appropriate to this phase included reviewing graphical depictions of the data, computing summary statistics, and comparing measurements across sensors. One well-known source of noise is a 60 Hz artifact in some of the measurements. This effect can easily be removed either by suppressing the relevant term in the frequency domain or by appropriate smoothing in the time domain. FIG. 11A shows the effects of this 60 Hz noise. FIG. 11B shows the much cleaner signal after the noise is removed.

Speaker Identification Analysis

We performed two classification analyses for speaker identification. The first classification algorithm used a conventional statistical approach where the feature space distance between subjects was determined by the Mahalanobis distance (although any error measurement and/or data correlation measurement technique may be used, both for speech biometric data as well as for cardiac and/or respiratory biometric data). The second classification was performed using cross-correlation as the feature space metric.

For the statistical classification, the temporal stream was segmented into discrete overlapping time frames. Mel-scale features were extracted from each time frame. Fundamentally, Mel-Scale attributes are the log-magnitude of the Fourier transform. Because the input stream was segmented into a number of frames, a large number of examples could be generated. This allowed us to not only perform classification, but also produce confidence intervals. The limitation of this analysis is that to provide a sufficient number of samples, the length of the segmented time frame will be short, resulting in possible differences between attributes extracted from the initial time frames to those to those collected at the end of the time series.

For the cross correlation, the log-magnitude of the Fourier spectrum was computed directly over the entire temporal stream. It is important to note that the two feature spaces are nearly identical. The Fourier spectrum was limited to either 512 or 1024 attributes. From these attributes, the cross correlation was computed for approximately the first 50 values. The limitation is based on the fact that the body resonances occur at lower frequencies than the vocalizations for communications. The advantage is that the integration over the entire temporal sequence ensures that attributes are derived from large samples which may provide more stable features. The limitation is that the only 1 sample exists for each vocalization, so a confidence interval is can not be determined directly.

Analysis of Heart Rate and Respiration Data

Figure 12:
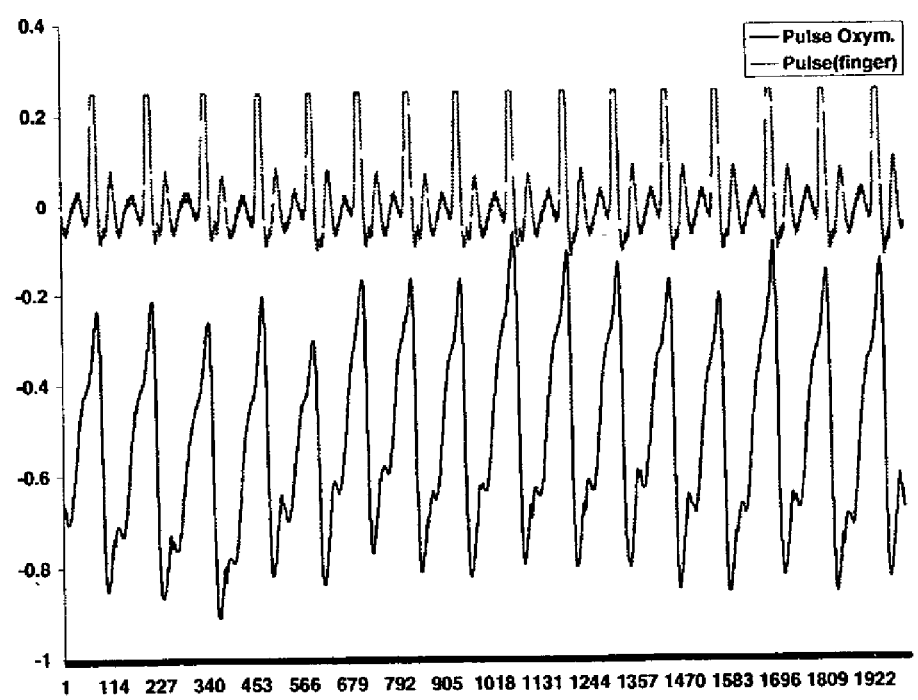
FIG. 12. Sample of pulse oximeter data and pulse measurements observed at the index finger.
Figure 13:
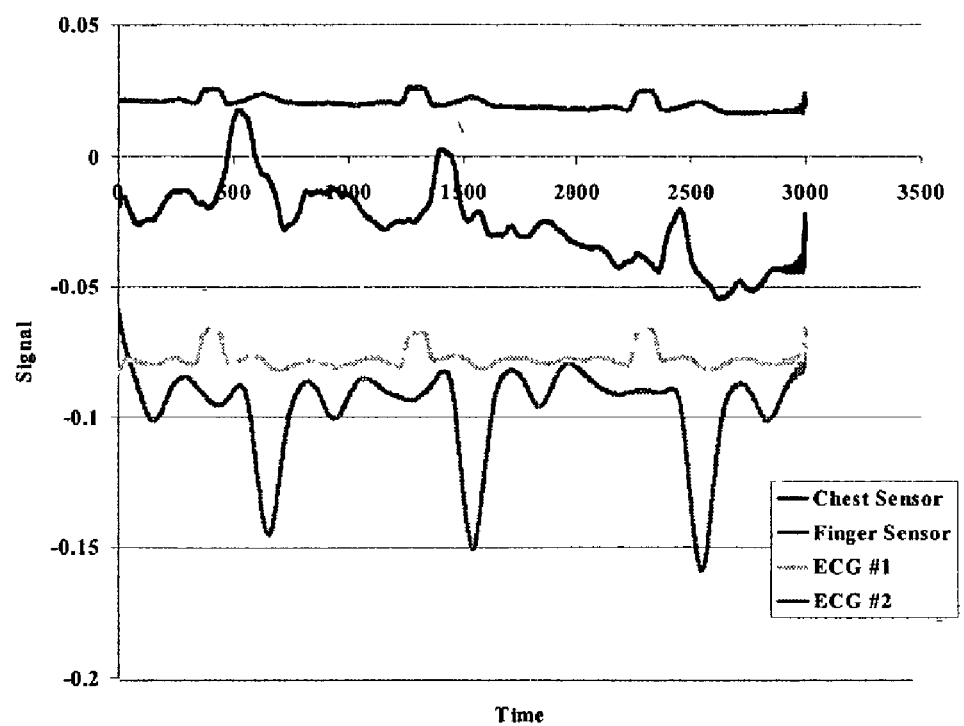
FIG. 13. Multiple measurements showing the relationship and time delays among electrical activity of the heart (ECG), the heart beat, and the pulse measured at the finger.

The non-acoustic data consisted of multiple measurements related to heart rate and respiration. Multiple measurements permit an assessment of data consistency, as well as indications of how the signal of interest might appear to other sensors. For example, two ECG measurements indicate the electrical activity that drives the heartbeat. In a sense, this is the purest measure of heart rate variability. Other measurements indicating activity of the heart include the pressure transducer sensor, which measures the mechanical activity of the heart, the pulse measurement at the finger, indicating the delayed effect of the heart beat in other parts of the body, and the pulse oximeter, which also shows the effect of the heartbeat, but through a different sensing-phenomenon. We observed strong correlations among these measurements (FIG. 12). In some cases, however, there were time lags related to the specific physiological processes and the locations of the sensor on the body. The R-wave in the ECG precedes the mechanical activity of the heart, which precedes the observed pulse in extremities like the finger (FIG. 13).

For both the heart rate and respiration data, the analysis treated the individual measurements as time series to be analyzed. Both time-domain and frequency-domain approaches were explored to identify robust, stable features for human identification. A cursory review of some preliminary data suggested that the signal associated with individuals differs in several respects. In the pulse oximetry data, for example, the height of the wave corresponding to the pulse is one feature, as is the interval between pulses.

Figure 14:
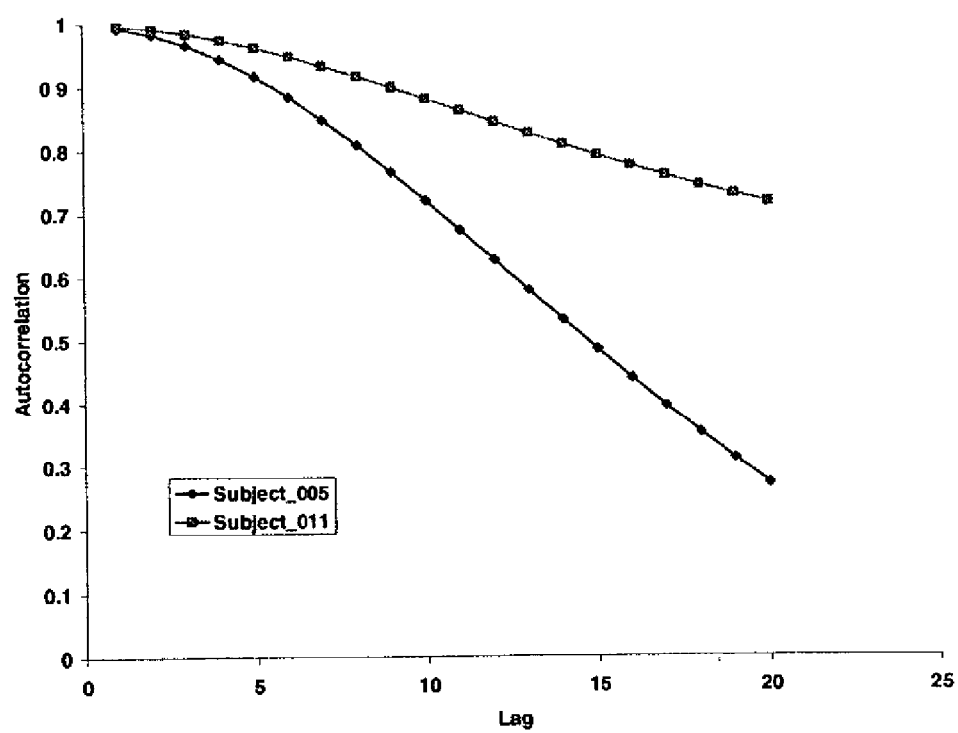
FIG. 14. Autocorrelations for a sample of pulse oximeter data.

However, the shape of the waveform is a more revealing attribute. Information about the shape of the pulse wave can be captured in the time domain through Auto Regressive Integrated Moving Average (ARIMA) modeling, which quantifies the temporal dependencies among the observations. Alternatively, the power spectrum captures equivalent information in the frequency domain. To illustrate, FIG. 14 shows the kth autocorrelations for k=1, . . . , 20 for roughly 20 seconds of pulse oximeter readings for two subjects. Note that the decay in the autocorrelation was much more rapid for subject 11 than for subject 5.

Biometric Features and Classification

For each of the sets of measurements—heart rate variability, respiration, and acoustic data, the goal of the initial analysis was to identify features that provide clear, robust separability across individuals. The second phase of the analysis was to characterize the behavior of these features and develop classification methods that exploit these features.

The choice of classification methods depends on the distribution of the data. Several procedures were tested, including statistical discriminant analysis. Performance was be measured using standard ROC analysis, and sources of misclassification were investigated by examining the confusion matrices. Comparisons of data for candidate individuals to reference data collected under a similar mental/emotional state (as represented by the tasks in the experiment) indicate identification performance under benign conditions. Comparisons across the tasks indicate the robustness of the biometric to the mental and emotional state of the candidate.

Because ROC analysis is a fundamental method for quantifying performance, it as useful to examine the derivation of the ROC curve. First, consider the verification task. In this case, a single "frame" of data corresponding to a single candidate is compared to a reference set of data for a single individual. If there is sufficient agreement between the two, a match is declared. Otherwise, a non-match is declared. Thus, there are two alternatives (match or non-match), and the decision rule chooses between the two. The required level of agreement is a threshold that can vary, giving rise to differing rates of true-positives and false positives. This is the classic ROC framework. The processes giving rise to detections and false alarms can be modeled as probability distributions and a host of statistical tools are available to estimate the ROC curve and draw inferences about performance.

The identification task differs somewhat, in that a single candidate is compared to a number of reference individuals to select a match. The individual could be classified correctly, classified as a different individual, or judged not to match anyone in the system. In this case, the classifier could make a number of incorrect decisions, and valuable diagnostic information resides in these specific misclassifications. The incorrect decisions can be pooled so that the data fit the two-class ROC framework, but information is lost in the process. In terms of the underlying processes, the misclassification score arises from the largest order statistic from a set of distributions, so care must be given to insure that the modeled ROC curve faithfully represents the observed performance. In our analysis we constructed ROC curves to provide summaries of performance and to facilitate comparisons, but we also present ed the detailed classification analysis.

EXAMPLE 8

Separability of Biometric Parameters Among Individuals

In this example, the relative intervals of the P, R, and T waves (FIG. 5) were extracted from a set of ECG data and used to compute the Mahalanobis distance among the samples (although, as discussed previously, other techniques may be used). Analysis of two-minute segments of ECG data from several subjects showed clear separability among the individuals (Table 9).

TABLE 9

Mahalanobis Distance Among Subjects, Based on Observed ECG Features

|  | Subject A | Subject B | Subject C | Subject D | Subject E |
|---|---|---|---|---|---|
| Subject A | −0.003 | −3.37 | −16.76 | −13.27 | −7.76 |
| Subject B |  | −0.007 | −30.93 | −8.03 | −18.91 |
| Subject C |  |  | −0.005 | −5.40 | −9.81 |
| Subject D |  |  |  | −0.001 | −12.01 |
| Subject E |  |  |  |  | −0.001 |

A similar analysis comparing the same features across the seven tasks within a single individual showed very little separation (Table 10).

TABLE 10

Mahalanobis Distance Among Tasks Within a Subject, Based on Observed ECG Features

|  | Task 1 | Task 2 | Task 3 | Task 4 | Task 5 | Task 6 | Task 7 |
|---|---|---|---|---|---|---|---|
| Task 1 | −0.001 |  |  |  |  |  |  |
| Task 2 | −4.077 | −0.029 |  |  |  |  |  |
| Task 3 | −0.618 | −0.138 | −0.003 |  |  |  |  |
| Task 4 | −0.254 | −0.231 | −0.128 | 0.000 |  |  |  |
| Task 5 | −1.964 | −1.823 | −2.390 | −1.790 | −0.001 |  |  |
| Task 6 | −5.155 | −3.597 | −4.345 | −3.856 | −2.346 | 0.000 |  |
| Task 7 | −1.834 | −2.471 | −3.146 | −1.696 | −3.117 | −29.014 | 0.000 |

This analysis indicates that features extracted from the ECG trace provide a method for identifying individuals, but appear to be stable within an individual. These findings demonstrate that heart rate variability is a viable biometric for identifying individuals.

EXAMPLE 9

Identification of Individuals by Pulse Oximetry

In this example, analysis of pulse oximetry data revealed that the shape of the wave corresponding to a single heartbeat is unique to the individual. As seen in FIGS. 15A and 15B, the average wave extracted from a short (12 second) segment of pulse oximeter data exhibits a stable shape within an individual, but varies among individuals.

A classification analysis indicated that individuals can be correctly identified using features extracted from the pulse oximeter signal. The feature extraction process followed these steps: (1) The autocorrelation function was computed to determine the periodicity of the signal. (2) Based on the time lag corresponding to the maximum autocorrelation, cycles arising from the individual heartbeats were extracted. (3) The time associated with each cycle was normalized to run from 0 to 1. (4) The scale of the signal was normalized to run from 0 to 1. (5) The normalized signal was then regressed on a polynomial function of the relative time; the estimated coefficients become the features for the classification analysis. Some or all of these steps may be performed in any combination or subcombination. Note that the normalization process removes absolute effects. In this example, only the shape information associated with the pulse oximeter signal is preserved. The regression analysis extracts features that capture these differences in the shape of the waves. A discriminant analysis (Morrison, D. F., *Multivariate Statistical Methods* (3rd ed.), McGraw-Hill (1990)) indicated that individuals can be classified based on these features, across all seven tasks where data were collected. Table 11 shows the classification results obtained during cross-validation (leave one out) and FIG. 15 depicts the data projected into the plane formed by the first two principle components.

TABLE 11

Classification results from cross-validation (leave one out)

| | | Predicted Group Membership | | |
|---|---|---|---|---|
| | | Subject A | Subject B | Subject C | Total |
| Actual Group Membership | Subject A | 6 (100%) | 0 | 0 | 6 |
| | Subject B | 0 | 7 (100%) | 0 | 7 |
| | Subject C | 0 | 0 | 7 (100%) | 7 |

EXAMPLE 10

Analysis of Existing Electrocardiographic Data

This example illustrates some of the information that can be extracted from the ECG data. ECG data obtained from the MIT-BIH database were analyzed to provide information about the temporal frequency of the heart rhythm. The temporal rhythm is a function of the individual and state of anxiety. In this initial study, we automatically extracted the peak in the electronic emission of the heart as the indicator of the heart beat (FIG. 5). Temporal changes, i.e., the time difference between R-R peaks, were visualized using different techniques. These visualizations provided insight to extract discriminators for intra-and inter-subject attributes.

Description of the Data

All of the data used for this initial study was taken from the MIT-BIH database. There is no extensive metadata describing the individuals. Personal communication with the investigator indicated that the patients used were ambulatory heart patients with or with out pace makers. The subjects were put under a physical stress during the recording.

The ECG data in this example was digital information with a data rate of 360 samples per second. The samples were taken from a 12 lead ECG hookup. The lead site for these subjects were not identified. Visually this data contains a high signal to noise. As such, no initial signal process or filtering was performed on the data.

Physiological Basis

Heart rate variability is the balance between the parasympathetic nervous system, which tends to slow heart rate, and the sympathetic nervous system, which tends to increase it. These changing rhythms affect a person's problem solving ability, decision making, and creativity. In the end, the balance affects how a person feels. Over time, the heart rate variability can be divided into frequency regions. Sympathetic activity changes are observed in the 0.003 to 0.04 Hz region, while parasympathetic changes can be seen in the 0.15 to 0.4 Hz region (Mateo and Laguna 2000).

For medical investigations, the goal is to understand the performance of the heart. The data is collected over long time periods approximately one day. In this manner, the analysts can evaluate temporal changes and heart reactions to changes in emotional state. Commonly these analyses are performed by computer code comparing local series to the patient's baseline and normal phenomena (Kundu et al. 2000). The analysts are observing the change in the distance between the R peaks of two heart beats, and the slope and duration of the individual waves within the heart beat.

Signal Processing

Direct observation shows that the peak of the R wave occurs within a very small interval of the heart beat; approximately $\frac{1}{25}$th of a second and appears to be independent of the RR interval. The magnitude of these peaks varies over time. However, the peak is generally greater than the other signal elements. To extract the R peak features, wavelets have been used to extract the QRS complex (Unser and Aldroubi 1996). Another technique is to model the entire ECG signal using temporal analysis (Mateo and Laguna 2000).

Description of the Relevant Features

After reviewing the data from a number of subjects, our strategy for finding the R peak was to look for the greatest voltage value in the region of the highest local variance. To do this, we selected 4 seconds of ECG data and computed the variance over each $\frac{1}{25}$th of a second. From this, the maximum variance was identified. A threshold was set that local R wave peaks will be within $\frac{1}{2}$ of this value. The process is repeated for every 4 seconds of data with a minor overlap to ensure a continuous datastream. This procedure effectively identifies the R peak in the data analyzed to date. However, tremendous differences exist between subjects, which tended to violate at least one of the processing assumptions. As such, our automated separation tended to miss or add about 1 beat in every 10 to 15 seconds of ECG data.

Peaks of R waves were determined as shown below:

```
{X : X is ECG Data}
{x : x is 4 seconds of X}
{v : v is the variance at all points x}
M = max(v)
{t : t > 0.5 * M}
{R : R = max(x, t)}
advance to the next overlapping interval
```

Figure 16A:
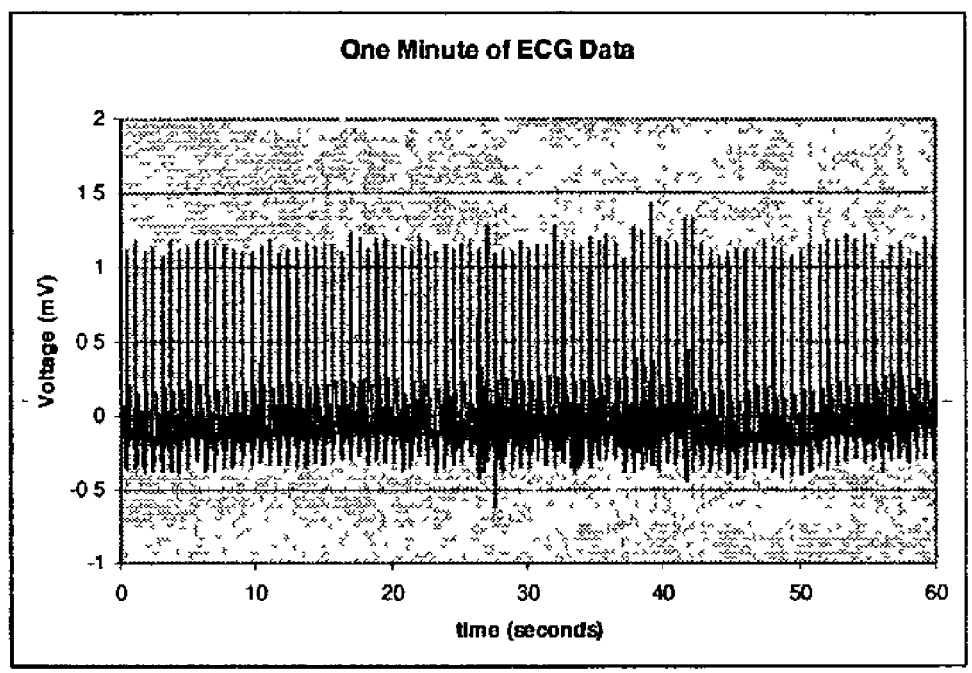
FIG. 16A, one minute of raw ECG data.
Figure 16B:
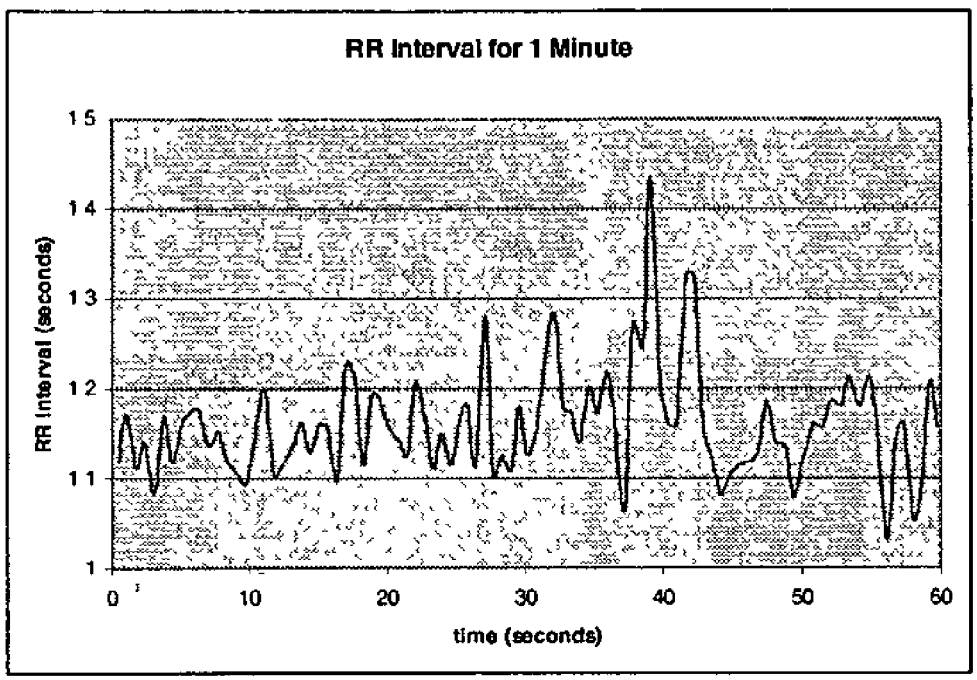
FIG. 16B, RR interval for one minute.

The results are shown in FIGS. 16A and 16B.

Separability Among Subjects

Figure 17A:
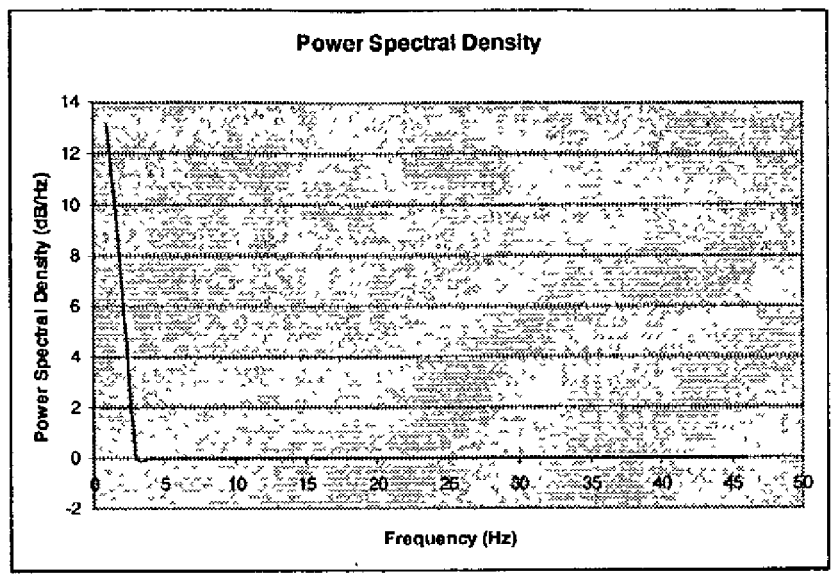
FIG. 17A, power spectral density from data in FIG. 16.
Figure 17B:
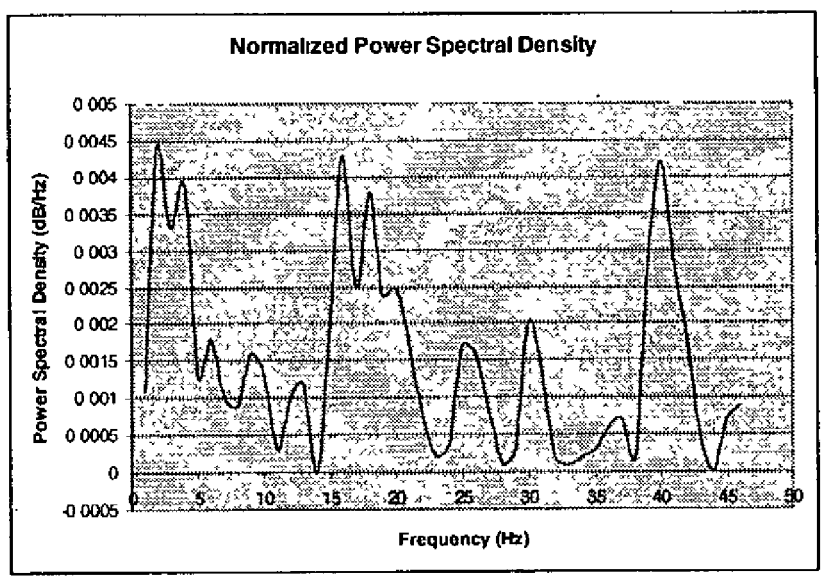
FIG. 17B, power spectral density with dc noise.

Preliminary analysis shows considerable differences among subjects; however, the lack of metadata limited detailed analysis. The data were put into a frequency analysis to determine the power spectral density. However, a very large de term dominated the results (FIG. 17A). The dc term was removed by subtracting the signal mean from each sample point prior to performing the frequency analysis. Once removed (FIG. 17B), several peaks were observed at very low signal values. The large dc term indicates that the temporal information is dominated by a static parameter in the data. Based upon the large dc term, a static statistical analysis should be reviewed to characterize the static information. In addition, heart beats occur on the order of 0.75–1 second.

Variability

Figure 18A:
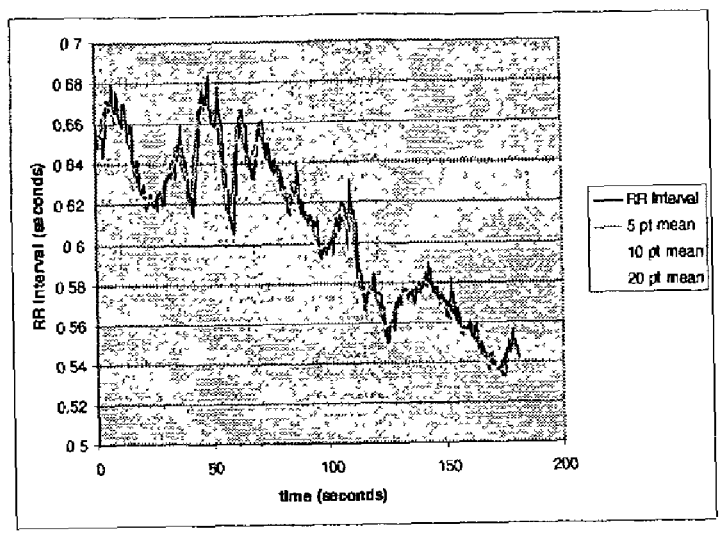
FIG. 18A, Subject 300.
Figure 18B:
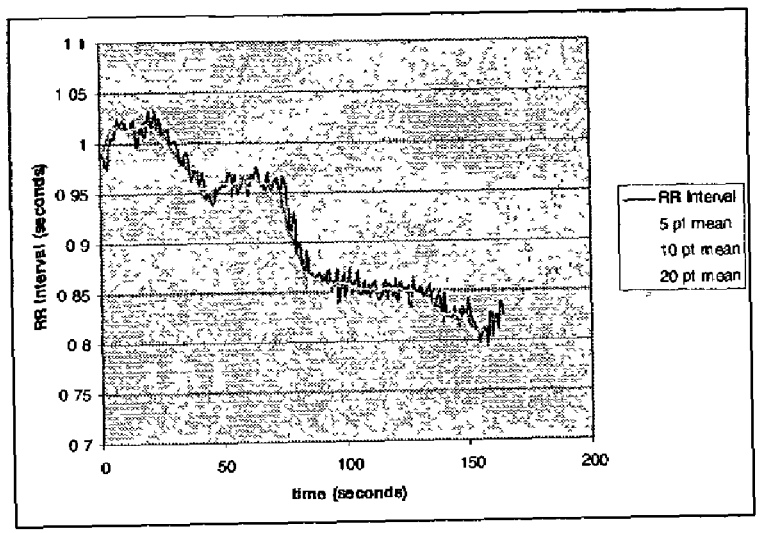
FIG. 18B, Subject 312.
Figure 18C:
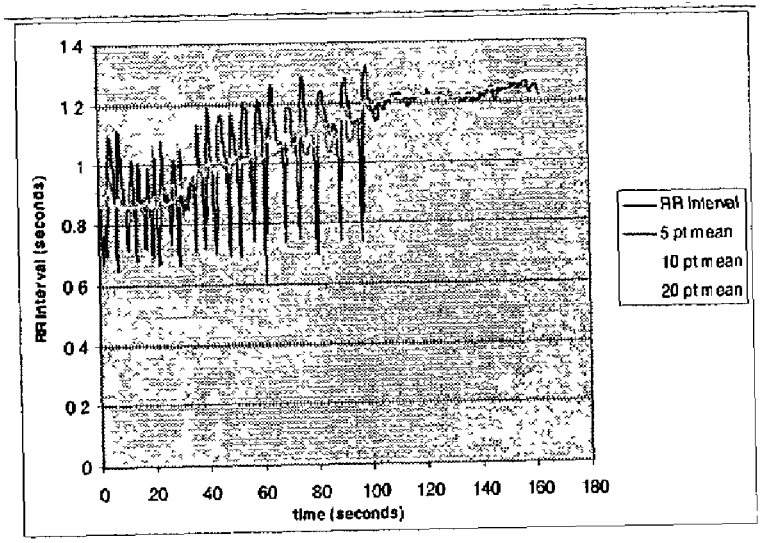
FIG. 18C, subject 324.
Figure 19A:
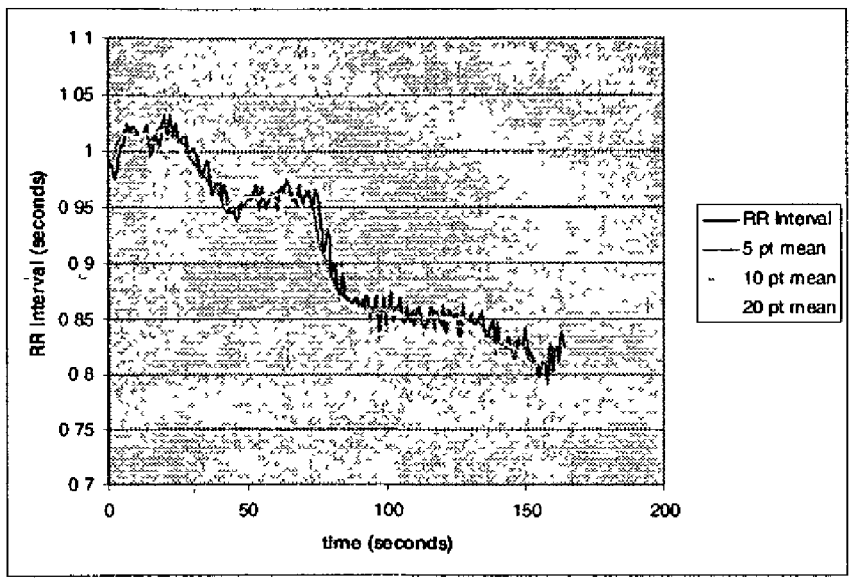
FIG. 19A, start of data.
Figure 19B:
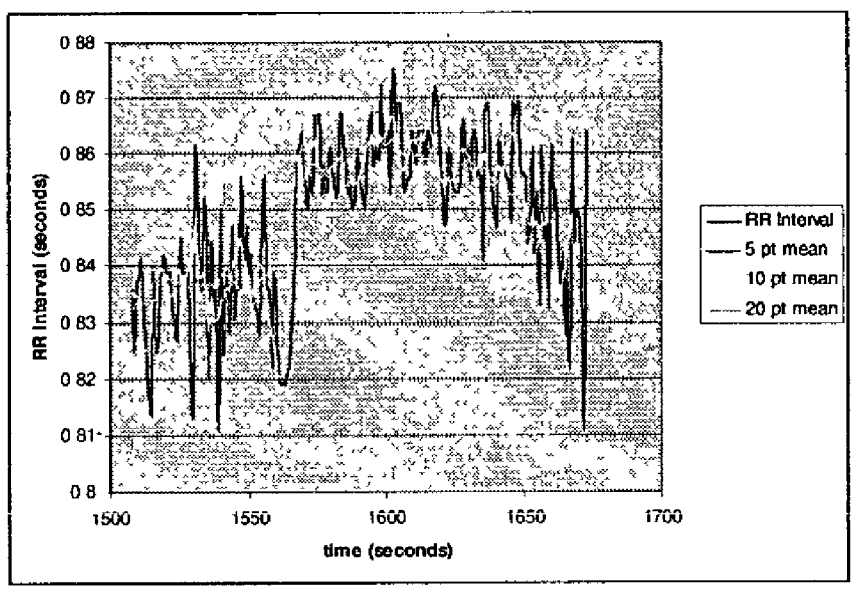
FIG. 19B, end of data, separated by 25 minutes.

Heart rate variability from 3 different subjects is shown in FIGS. 18A-C, respectively. A brief investigation shows substantial variation within a single subject (FIGS. 19A, 19B).

Data Characterization

Figure 20A:
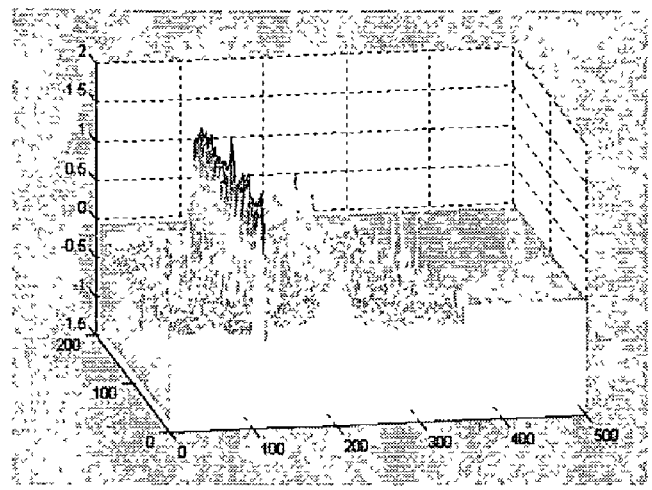
FIG. 20A, subject 300.
Figure 20B:
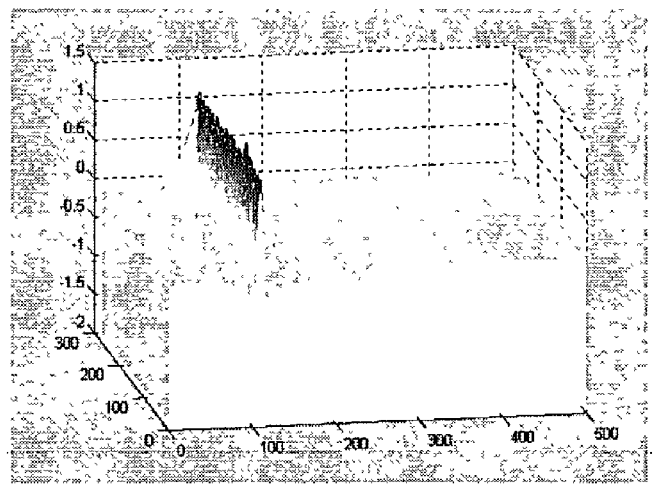
FIG. 20B, subject 312.
Figure 20C:
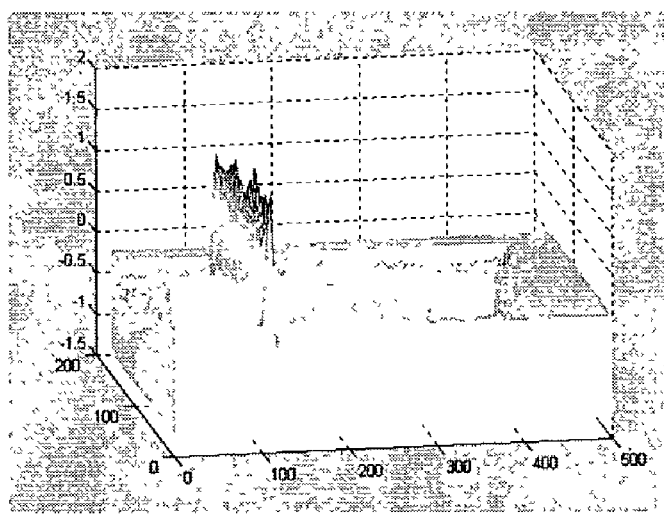
FIG. 20C, subject 324.

Another way to visualize this information is through the use of waterfall diagrams. If we stacked the information temporally and align the R wave peaks by heart beat, the overall shape of the ECG signal is evident. See FIGS. 20A–20C.

EXAMPLE 11

Speaker Recognition Analysis

In this example, the objective of speaker recognition analysis was to identify individuals based upon the fundamental frequencies of their vocalizations. Speaker recognition has received a considerable amount of exposure in the academic literature. Our procedures and analysis tools have an experimental as well as theoretical basis. In this example, we compared the commonly used Mel-scale cepstrum coefficients within a Bayesian classifier to Power Spectral Density attributes using "template" matching.

Background

Figure 21A:
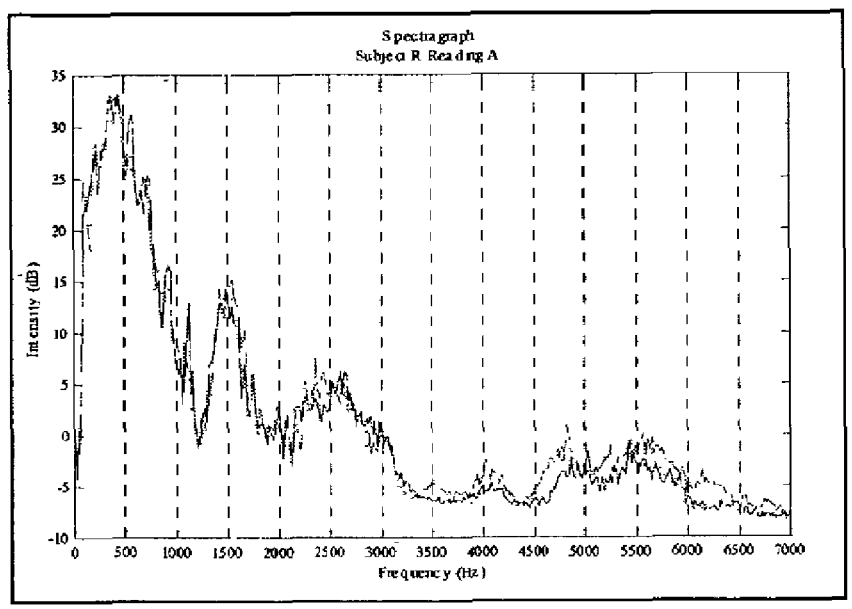
FIG. 21A, subject R.
Figure 21B:
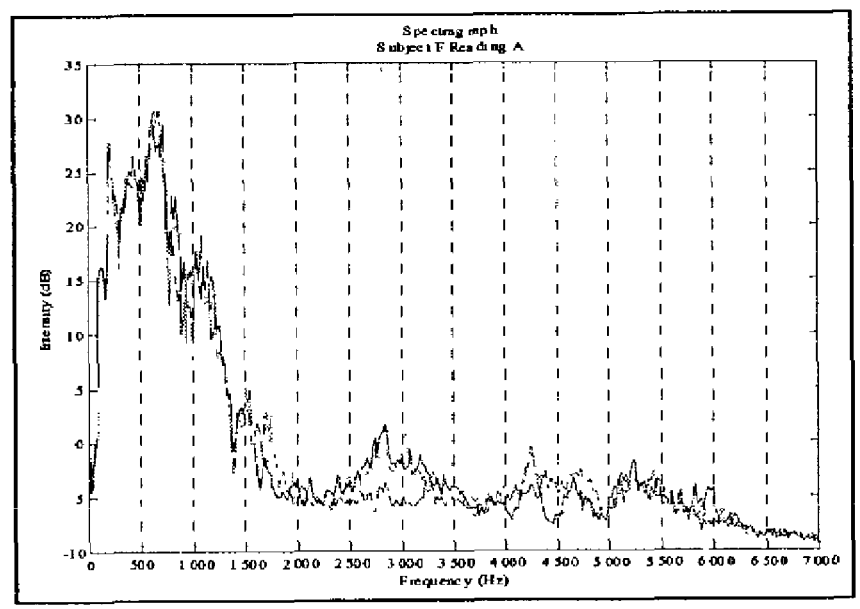
FIG. 21B, subject F.

During vocalizations, a range of frequency signals is produced. These are recorded as intensity values, usually as volts, at regular time intervals. Speech data is most commonly collected at 11.05 kHz or 22.05 kHz. At these data rates, the high frequency information associated with specific words and the low frequency information associated with an individual physiology are resolved. Unlike high frequency data, the low frequency information is not expected to vary with time (Doddington 1985). To characterize an individual by their vocalizations, the data stream is often transformed and analyzed in the frequency space. FIGS. 21A and 21B show the log magnitude time frequency spectra from two individuals speaking identical phrases. Considerable differences can be observed between the curves at the lower frequencies (to the left of the graphs).

The two different analyses applied here highlight the limitations in the data. Temporally segmenting the vocalization stream allows the analysis to develop parametric statistics and determine error bounds for expected performance. However, these temporal segments contain an unknown distribution based upon language, culture, state of anxiety, and spoke content. The power spectrum information is collected across the entire datastream. The advantage is that the temporally variable components are minimized relative to the natural body resonance. However, the single feature vector does not provide enough samples to develop sufficient information to develop error bounds and expected performance characteristics.

Mel-Scale

To ensure that an individual's fundamental frequency is captured, the temporal signal is segmented. The segments are taken over multiple phonemes, where a phoneme is the smallest element of speech. Due to the high data rate and interest only in the low frequency information, feature extraction is performed on the individual segments. We extracted Mel-scale cepstral features as attributes for speaker recognition. The Mel-scale operator takes the log of the magnitude of the frequency spectrum over temporal segments or "frames." Computation of Mel-scale attributes is carried out as follows:

$$\text{Mel} - \text{scale(segment)} = (\log|\text{FFT(frame)}|)$$

This has the effect of reducing the emphasis of the higher frequencies on the system. The process is based on the non-linear audio perception of humans (Furui 1981).

One considerable advantage of this type of processing is that Mel-scale attributes are often modeled by multivariate Gaussian distributions as shown below:

$$\text{Mahalanobis Distance} = (\bar{x} - \mu)' \Sigma^{-1} (\bar{x} - \mu)$$

where:
$\bar{x}$ = mean test vector
$\mu$ = mean training vector
$\Sigma$ = covariance of training vector Mahalanobis distance is only one possible measurement technique that may be used to classify utterances to speakers.

Power Spectrum

The power spectrum of the entire vocalization stream was computed. From the time series, the data was converted to the frequency domain using 1024-parameter Fourier Transform. The fixed number of parameters performed two functions. It normalized the datastreams and makes the analysis more computationally tractable by limiting the number of variables. The square of the Fourier magnitude was computed and the log of all attributes was derived. Euclidean distances were derived between individual attribute vectors as follows:

Log Power Spectrum = log|FFT(Vocal Stream)|

Description of the Data

For this analysis, we collected the data at 22.05 kHz. The data were collected using a non-contact microphone and due to noise in the system, it is expected that the highest resolvable signal will be considerable less. The subjects hummed into the microphone through a continuous increasing then decreasing range over approximately 1 ½octaves. Three unique trials were obtained for each subject. No stresses were placed on the individuals. In this case, the subjects were middle aged males.

Physiological Basis

Speaker recognition has a physiological basis. The length of the vocal cords, size of the nasal cavity, and size of the chest cavity all effect the fundamental spoken and non-spoken resonances of an individual. During speech, air is forced through the vocal chords that produce periodic pulses that are filtered by the vocal tract and the individual's physiology. For human identification, the structure of the individual is difficult if not impossible to mask. In addition, a secondary acoustical effect is currently being studied that links the emotional state of the target with their voice pattern (Fox 2000).

Results of the Analysis

Figure 22A:
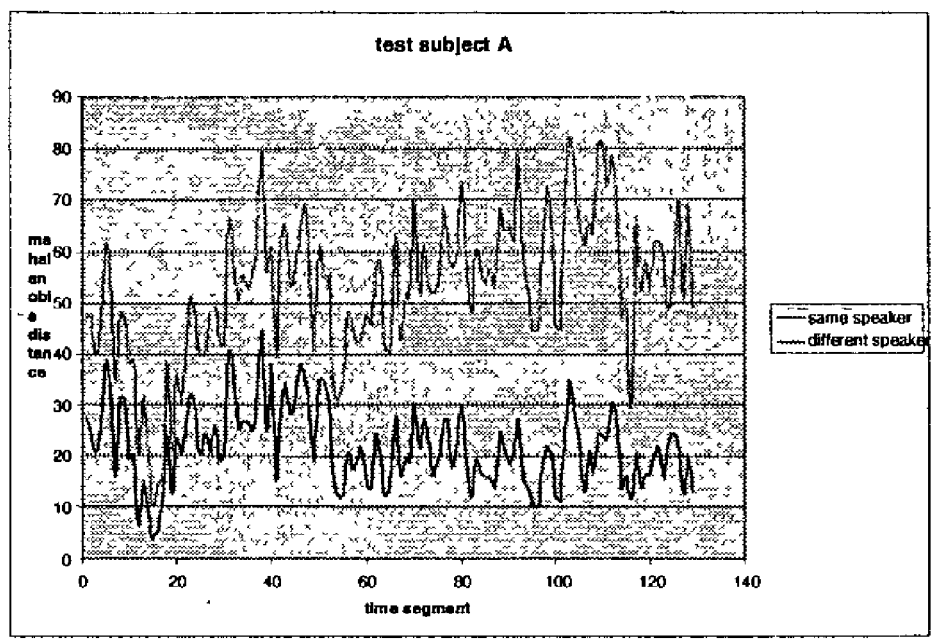
FIG. 22A, distance between test data of both test subjects "A" and "B" with the training data of test subject "A.
Figure 22B:
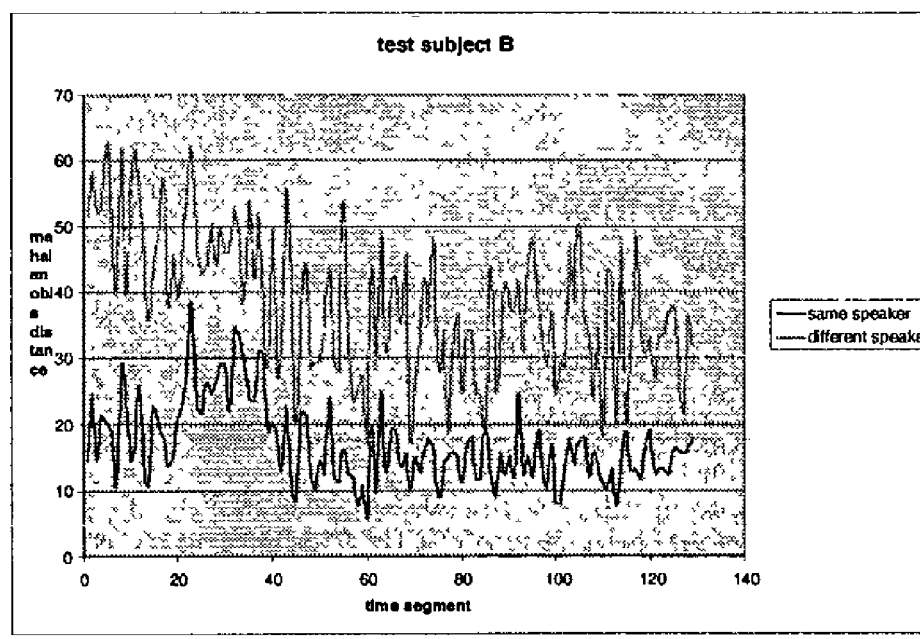
" FIG. 22B, distance between test data of both test subjects "A" and "B" with the training data of test subject "B."
Figure 23A:
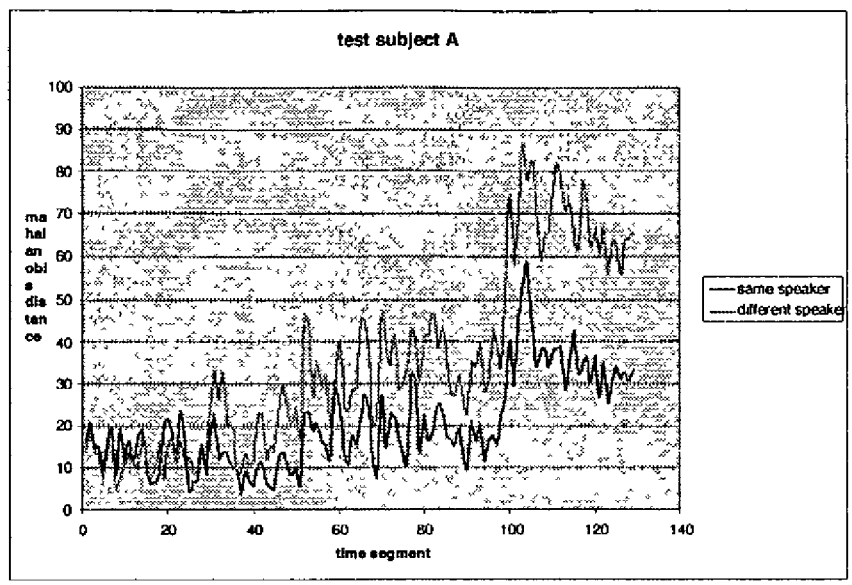
FIG. 23A, distance between test data of both test subjects "A" and "B" with the training data of test subject "A.
Figure 23B:
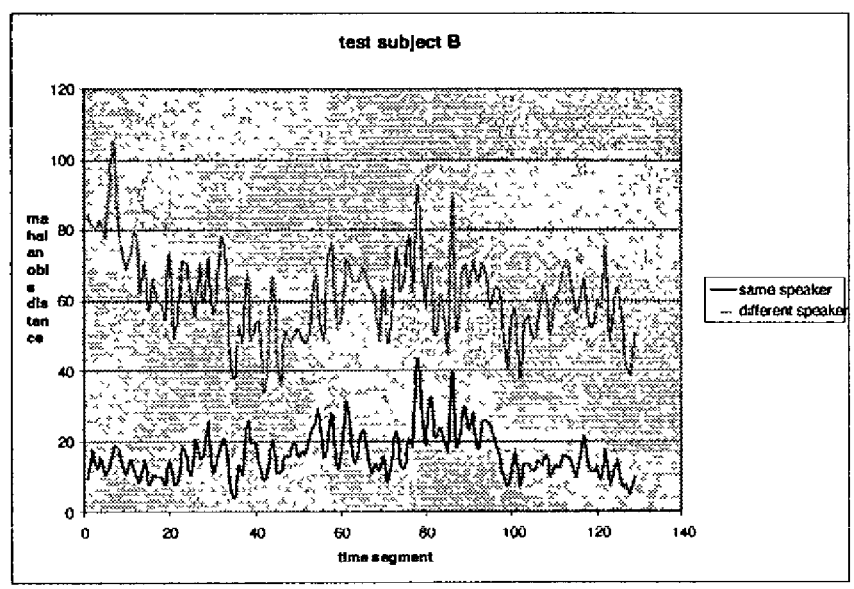
" FIG. 23B, distance between test data of both test subjects "A" and "B" with the training data of test subject "B."
Figure 24A:
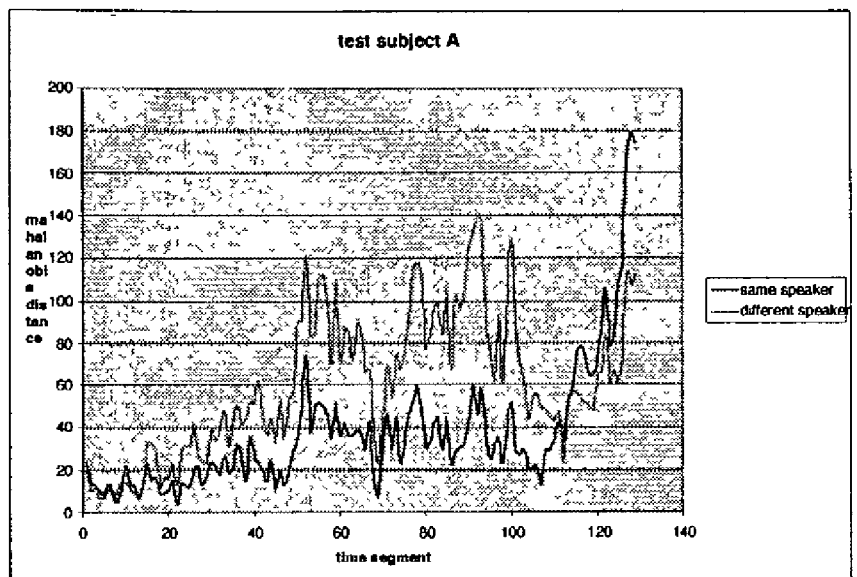
FIG. 24A, distance between test data of both test subjects "A" and "B" with the training data of test subject "A.
Figure 24B:
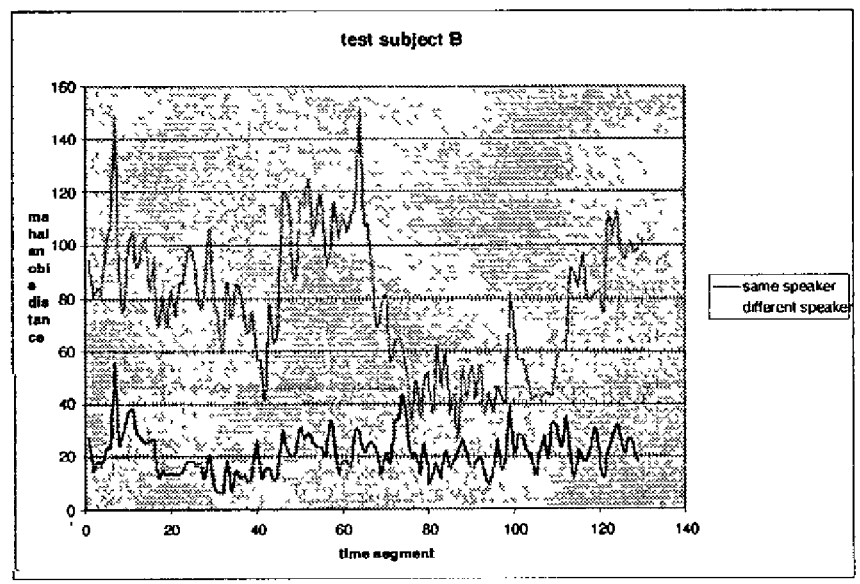
" FIG. 24B, distance between test data of both test subjects "A" and "B" with the training data of test subject "B."

Mel-Scale Ceptrum. The total datastream contained approximately 20 seconds of speech per trial. Two of the three trials were analyzed for both individuals. The data segments were approximately 20 ms. This created approximately 30 samples for analysis. A separate trial was used to generate approximately 30 independent test samples. The results are shown in FIGS. 22, 23, and 24.

The graphs of separability (FIGS. 22, 23, and 24) were generated using Mahalanobis distance as a discriminator. The top graph in each set is the distance between test data of both Subject 1 and Subject 2 with the training data of Subject 1. The bottom graph in each set is the distance between the test data of both Subject 1 and Subject 2 with the training data of Subject 2. In both cases, the lighter line drawn is with different training and test subjects and the darker line is the same training and test subject. In all cases, the information used was acquired independently.

The smaller the Mahalanobis distance between the training and test data the more similar the data are. The graphs are plots of Mahalanobis Distance versus segment. The three sets of graphs were created at different segmentation rates.

The results by using Speaker 2 as training (the right hand graphs) appear as expected, where the Mahalanobis Distance between the same person and different person increased with increasing segmentation rate. This indicates that the longer integration time improves the characterization of an individual. The left graphs appear to contain sufficient noise in the training data.

Power Spectrum Attributes

The power spectrum is determined as the square the Fourier magnitude. The total number of frequencies available is ½the entire number of samples. Our Fourier transformation applied the entire raw dataset to 1024 frequencies. From this, the $\log_{10}$ of the power spectrum was computed.

The results are shown in Table 12.

TABLE 12

Template Matching Power Spectral Density of Two Speakers

| Average Distance $\log_{10}$ (power) | subject 1A | subject 1B | subject 2 |
|---|---|---|---|
| subject 1A | 2.59 | 4.61 | 11.59 |
| subject 1B |  | 3.00 | 8.56 |
| subject 2 |  |  | 1.66 |

The distance measures are the absolute value of the differences for the first 22 frequencies. The goal was to observe the relationship between the within subject variation and between subject variation. Table 11 shows that the intra-subject variation is considerable less, approximately half, than the inter-subject variation. The subject 1A and subject 1B value are a single subject reading from Text A and Text B. The Subject 2 values are a different subject reading from Text A.

Various embodiments and aspects of the present invention have been described above, and it will be understood by those of ordinary skill that the present invention includes within its scope all combinations and subcombinations of these embodiments and aspects. For instance, it is conceived that the subjects from which biometric data may be measured are not limited to humans but may further include animals such as race horses, tracking animals, including dogs, and/or other valuable animals. The full scope of the present invention should only be limited by the claims.

REFERENCES

Bou-Ghazale, S. E. and Hansen, J. H. L. 2000. A Comparative Study of Traditional and Newly Proposed Features for Recognition of Speech Under Stress, IEEE Transactions on Speech and Audio Processing, 8(4):429–442.

Congalton, R. G. and Green, K. 1993. A Practical Look at the Sources of Confusion in Error Matrix Generation, Photogrammetric Engineering and Remote Sensing, 59(5):641–644.

Doddington, G. R. 1985. Speaker Recognition—Identifying People by their Voices, Proceedings of the IEEE, 73(11): 1651–1664.

Fox, B. 2000. Reading Between the Words, New Scientist, (23 September):7.

Furui, S. 1981. Cepstral Analysis Technique for Automatic Speaker Verification, IEEE Transactions on Acoustics, Speech, and Signal Processing, ASSP-29(2):254–272.

Greneker, E. F., 1997. Radar Sensing of Heartbeat and Respiration at a Distance with Applications of the Technology, Radar 97, 14–16 Oct. 1997, pp.150–154.

Juang, B. H. 1998. The Past, Present, and Future of Speech Processing, IEEE Signal Processing Magazine, 15(3): 24–48.

Hall, D. L. 1992. Mathematical Techniques in Multi-sensor Data Fusion, Artech House, Inc., Norwood, Me.

Khamene, A. and Negahdaripour, S. 2000. A New Method for the Extraction of Fetal ECG from the Composite Abdominal Signal, IEEE Transactions on Biomedical Engineering, 47(4):507–516.

Kundu, M., Nasipuri, M., and Basu, D. K. 2000. Knowledge-Based ECG Interpretation: A Critical Review, Pattern Recognition, 33(3):351–373.

Lagerholm, M., Peterson, C., Braccini, G., Edenbrandt, L., and Sornmo, L. 2000. Clustering ECG Complexes Uinsg Hermite Functions and Self-Organizing Maps, IEEE Transactions on Biomedical Engineering, 47(7):838–848.

Masters, T. 1994. Signal and Image Processing with Neural Networks: A C++ Sourcebook, John Wiley and Sons, Inc., New York.

Mateo, J. and Laguna, P. 2000. Improved Heart Rate Variability Signal Analysis from the Beat Occurrence Times According to the IPFM Model, IEEE Transactions on Biomedical Engineering, 47(8):985.

Morrison, D. F. 1990. Multivariate Statistical Methods (3rd ed), McGraw-Hill.

Unser, M. and Aldroubi, A. 1996. A Review of Wavelets in Biomedical Applications, Proceedings of the IEEE, 84(4): 626–638

Task Force of the European Society of Cardiology and the North American Society of Pacing and Electrophysiology. 1996. Special Report: Heart Rate Variability Standards of Measurement, Physiological Interpretation, and Clinical Use, Circulation, 93(5):1043–1065.

Yoshiya, I., Shimada, Y., and Tanaka, K. 1980. Spectrophotometric Monitoring of Arterial Oxygen Saturation in the Fingertip, Med. Biol. Eng. Comput., 18:27–32.

What is claimed is:

1. A method of identifying a subject, comprising steps of:
    (a) comparing a first and a second set of biometric parameters extracted from a heart rate variability measurement, wherein
        (1) the first set of biometric parameters is associated with a first subject, and
        (2) the second set of biometric parameters is associated with a second subject; and
    (b) identifying the first subject as the second subject if the first set and second set correlate, and identifying the first subject as different from the second subject if the first and second sets do not correlate.

2. The method of claim 1 further comprising the step of analyzing the heart rate variability measurement of the first subject to extract the first set of biometric parameters.

3. The method of claim 2 further comprising the step of acquiring the heart rate variability measurement from the first subject.

4. The method of claim 1 wherein the first set of biometric parameters is compared to a plurality of second sets of biometric parameters, wherein individual members of the plurality are each associated with a different, third subject.

5. The method of claim 1 further comprising applying a low pass filter to the heart rate variability measurement.

6. The method of claim 5 wherein the low pass filter is a 40 Hz low pass filter.

7. The method of claim 1 wherein the heart rate variability is measured using a standoff measuring technique.

8. A method of compiling a database comprising sets of biometric parameters each associated with an individual subject, comprising steps of:
    (a) acquiring heart rate variability measurements from a plurality of individual subjects;
    (b) analyzing the heart rate variability measurements to extract sets of biometric parameters, wherein each set of biometric parameters is associated with an individual subject; and
    (c) compiling the sets of biometric parameters into a database, wherein individual sets of biometric parameters are each correlated with the individual subjects from which the heart rate variability measurements were obtained.

9. The method of claim 8 further comprising applying a low pass filter to the heart rate variability measurements.

10. The method of claim 9 wherein the low pass filter is a 40 Hz low pass filter.

11. A method for identifying a subject according to a periodic physiological process of the subject, the method comprising steps of:
    measuring the periodic physiological process for a period of time to generate biometric data, the period of time being sufficient such that the biometric data contains data corresponding to a plurality of cycles of the physiological process;
    extracting a plurality of the cycles of the biometric data; and
    estimating a first plurality of coefficients based on the plurality of cycles.

12. The method of claim 11, further including the step of determining a periodicity of the biometric data.

13. The method of claim 11, further including the step of normalizing the plurality of cycles, the step of estimating including estimating the plurality of coefficients based on the plurality of normalized cycles.

14. The method of claim 11, wherein the periodic physiological process is a heartbeat or pulse.

15. The method of claim 11, wherein the periodic physiological process is respiration.

16. The method of claim 11, wherein the step of estimating includes regressing the cycles on a polynomial function over time.

17. The method of claim 11, further including the step of comparing the first plurality of coefficients with a second plurality of coefficients.

18. The method of claim 11 wherein the periodic physiological process is measured using a standoff measuring technique.

19. A method for identifying a subject according to heart activity of the subject, the method comprising the steps of:
    measuring the heart activity over a period of time sufficient so as to include a plurality of heartbeats to generate heart activity data;
    aligning heart activity data corresponding to each of the plurality of heartbeats; and
    identifying the subject according to the heart activity data.

20. The method of claim 19, further including the step of identifying at least one feature of the heart activity data, the method of identifying including identifying the subject according to the at least one feature.

21. The method of claim 19, further including the step of applying a lowpass filter to the heart activity data.

22. The method of claim 21, wherein the lowpass filter is a 40 Hz lowpass filter.

23. The method of claim 19 wherein the heart activity is measured using a standoff measuring technique.

24. A method for identifying a subject according to respiration of the subject, the method comprising steps of:
    measuring the respiration to generate respiration data, wherein the respiration data includes a temperature change associated with inhalation and exhalation of the subject; and
    identifying the subject based on the respiration data.

25. The method of claim 24, wherein the step of measuring includes measuring the respiration using a standoff measuring technique.

26. The method of claim 24 further comprising applying a low pass filter to the respiration data.

27. The method of claim 26 wherein the low pass filter is a 40 Hz low pass filter.

28. A method for identifying a subject according to at least one of a cardiac and a respiratory physiological process of the subject, the method comprising steps of:
    measuring the physiological process to generate biometric data;
    estimating a coefficient from the biometric data; and
    identifying the subject according to the coefficient.

29. The method of claim 28 further comprising applying a low pass filter to the biometric data.

30. The method of claim 29 wherein the physiological process is a cardiac process and the low pass filter is a 40 Hz low pass filter.

31. The method of claim 29 wherein the physiological process is a respiratory process and the low pass filter is a 60 Hz low pass filter.

32. The method of claim 28 wherein the physiological process is measured using a standoff measuring technique.

* * * * *